(12) United States Patent  (10) Patent No.: US 7,849,610 B2
Clough  (45) Date of Patent: Dec. 14, 2010

(54) ORTHOPEDIC SHOE APPLIANCE AND METHOD

(76) Inventor: James G. Clough, Cluffy Biomedial LLC, 3700 Huckleberry Dr., Great Falls, MT (US) 59404

( * ) Notice: Subject to any disclaimer, the term of this patent is extended or adjusted under 35 U.S.C. 154(b) by 915 days.

(21) Appl. No.: 11/367,205

(22) Filed: Mar. 3, 2006

(65) Prior Publication Data
US 2007/0204487 A1   Sep. 6, 2007

(51) Int. Cl.
A61F 5/14   (2006.01)
A43B 13/12   (2006.01)

(52) U.S. Cl. .................... 36/71; 36/140; 36/43
(58) Field of Classification Search .......... 36/71, 36/140, 94, 43
See application file for complete search history.

(56) References Cited

U.S. PATENT DOCUMENTS

| 893,876 | A | * | 7/1908 | Schuktz | 128/894 |
| 2,888,013 | A | * | 5/1959 | Levitt | 128/894 |
| 3,063,446 | A | * | 11/1962 | Levitt | 602/30 |
| 3,548,420 | A | * | 12/1970 | Spence | 623/37 |
| 4,263,902 | A | | 4/1981 | Dieterich | |
| 4,333,472 | A | | 6/1982 | Tager | |
| 4,408,402 | A | | 10/1983 | Looney | |
| 4,414,964 | A | | 11/1983 | Farino et al. | |
| 4,644,941 | A | * | 2/1987 | Ogle, II | 602/22 |
| 4,852,553 | A | | 8/1989 | Voykin | |
| 4,940,046 | A | * | 7/1990 | Jacoby | 602/30 |
| 5,183,458 | A | * | 2/1993 | Marx | 602/22 |
| 5,230,699 | A | * | 7/1993 | Grasinger | 602/22 |
| 5,330,391 | A | * | 7/1994 | Mitchell | 473/59 |
| 5,694,705 | A | | 12/1997 | Alonso Coves | |
| 5,881,478 | A | | 3/1999 | McMahon et al. | |
| 6,092,314 | A | | 7/2000 | Rothbart | |
| 6,170,176 | B1 | | 1/2001 | Clough | |
| 6,182,380 | B1 | | 2/2001 | Liley | |
| 6,412,198 | B1 | * | 7/2002 | Rothbart | 36/144 |
| 6,513,264 | B2 | * | 2/2003 | Sinaie | 36/43 |
| 6,874,258 | B2 | | 4/2005 | Clough et al. | |
| 6,938,363 | B1 | | 9/2005 | Clough | |
| 2006/0069334 | A1 | * | 3/2006 | Moskowitz | 602/5 |

FOREIGN PATENT DOCUMENTS

WO   WO 9200714 A1 *  1/1992

* cited by examiner

Primary Examiner—Marie Patterson
(74) Attorney, Agent, or Firm—Osha • Liang LLP

(57) ABSTRACT

An orthopedic appliance includes a slab configured to be placed underneath a big toe, forward of and not extending under a head of a first metatarsal, and wherein the slab has a predetermined height and is configured to deflect a proximal phalanx upwardly relative to the first metatarsal. A method for improving stability of a foot during ambulation includes placing an orthopedic appliance, having a predetermined height, under a big toe such that the orthopedic appliance is located forward of and does not extend under a head of a first metatarsal of the big toe; and deflecting a proximal phalanx upwardly relative to the first metatarsal.

15 Claims, 22 Drawing Sheets

ORTHOPEDIC SHOE APPLIANCE AND METHOD

CROSS-REFERENCE TO RELATED APPLICATIONS

This application is related to application Ser. No. 10/032,604, now U.S. Pat. No. 6,874,258, issued on Apr. 5, 2005, which is a continuation-in-part of application Ser. No. 09/693,235, filed on Oct. 20, 2000, now U.S. Pat. No. 6,938,363, issued on Sep. 6, 2005, which is a continuation-in-part of application Ser. No. 09/467,973, filed on Dec. 21, 1999, now U.S. Pat. No. 6,170,176, issued on Jan. 9, 2001.

BACKGROUND OF THE INVENTION

1. Field of the Invention

The invention relates generally to orthopedic corrective devices and methods.

2. Background Art

When a person ambulates, or moves from place to place such as by walking, a host of triplane motions occur to the foot structure, broadly termed pronation and supination. Pronation of the foot generally involves a depression of the arch, mobility of the foot and an internal rotation of the leg. Supination generally involves an elevation of the arch and stability of the foot structure with external rotation of the leg. When a person over-pronates, or for any other reason places too much force on the inside of the foot, excessive mobility of the medial arch area of the foot can result. The resulting foot instability can be manifested as arch, foot, ankle, and/or leg pain, as well as postural problems from excessive internal rotation of the leg.

Conventional orthopedic corrective devices described to address this problem include many different types. However, none provide for an orthopedic shoe appliance specifically adapted to provide improved stability of the foot structure, and a method of providing for improved stability of the foot structure, during ambulation in the manner which is provided for in the present invention.

U.S. Pat. No. 6,182,380, issued Feb. 6, 2001 to Liley teaches a small pad in the general shape of a common big toe to be inserted in the insole as a support for the big toe. The pad is designed to correct for the varum forefoot deformity of a short first metatarsal bone. The pad extends from the tip of the big toe to a point behind the metatarsal parabola.

U.S. Pat. No. 6,092,314 issued Jul. 25, 2000 to Rothbart discloses a foot support system that includes a bed upon which the foot rests. The foot support system is positioned underneath the medial column of the forefoot of foot. The foot support system laterally decreases in thickness from the inner edge to the outer edge. The inner edge is positioned along the medial side of the foot, and the outer edge is positioned longitudinally in a zone adjacent to a lateral margin of the hallux, the proximal phalanx, and the first metatarsal and a medial margin of the phalanges of the second toe and the second metatarsal.

U.S. Pat. No. 5,881,478, issued Mar. 16, 1999 to McMahon et al. teaches a shoe having a resilient sole, an upper secured to the sole, and a rockable member within a cavity in the sole. The rockable member being configured for side-to-side rocking in the sole cavity between a neutral position and a tilted position as the wearer's foot is moved relative to the sole between a neutral position as the wearer's foot is moved relative to the sole between a neutral position and a tilted position.

U.S. Pat. No. 5,694,705, issued Dec. 9, 1997 to Alonso Coves teaches an insole formed by the combination of two laminar bodies, one of split leather and the other of rubber material being provided with knobs forming support projections for the foot.

U.S. Pat. No. 4,852,553, issued Aug. 1, 1989 to Voykin teaches a foot zone reflex self-administering therapy apparatus comprising a display board adapted to display foot reflexology zones corresponding to anatomical areas of the body and stimulating members adapted to be placed on the display board at a zone corresponding to an anatomical area of the body requiring therapy.

U.S. Pat. No. 4,414,964, issued Nov. 15, 1983 to Farino et al. teaches a post-operative pliable protector device for the hallux or big toe having a cushion pad with at least a portion thereof adapted to encircle the toe and being formed with a separable fastener having a loop-type fabric.

U.S. Pat. No. 4,408,402 issued Oct. 11, 1983 to Looney teaches a supportive shoe or insert which provides increased support to specific areas of the foot during the first, second and third trimesters of pregnancy to compensate for changes in body weight and center of gravity. A pad, which can be a shoe insole, is provided with these specific areas of support.

U.S. Pat. No. 4,333,472, issued Jun. 8, 1982 to Tager teaches compensatory-corrective orthopedic foot devices comprising of the construction and specific application of a series of differentially-sized geometrically-shaped and specifically configured, generally wedge-shaped, prosthetic devices that are utilized in the compensatory treatment of specific clinical structural biomechanical abnormalities of the human foot.

U.S. Pat. No. 4,263,902, issued Apr. 28, 1981 to Dietrich teaches an orthopedic sandal for correction of hammer-toes and X-toe comprising a dual lever arm arrangement pivotable on a horizontal axis transverse to the sole. Additionally, a pressure element for pressing the toes downward in on one arm and the other arm is fastened to the rearward portion of the foot so that as the foot is lifted, the pressure element is pressed downwardly on the hammer-toes.

None of the art as identified above, either individually or in combination, describes an orthopedic appliance or a method, which specifically provides for improved stability of the foot structure during ambulation. Many individuals suffer from a functional limitation of the hallux, (big toe) motion with ensuing joint pathology and pain. Additionally, many people suffer from abnormal weight distribution on the ball of the foot with lesser metatarsalgia complaints. Over-pronation can be a contributing factor to a host of other foot ailments as well as contributing to abnormal mechanics of the ankle, knee, hip and lower back. This problem is common and has been a topic of concern by shoe manufacturers and podiatrists attempting to achieve foot comfort. However, the prior art has not accomplished improving both stability and comfort during ambulation.

BRIEF SUMMARY OF THE INVENTION

The invention relates to a method and apparatus for improving stability of the foot structure during ambulation. In one aspect, the invention relates to an orthopedic appliance, which includes a slab configured to be placed underneath a big toe forward of and not extending under a head of a first metatarsal, and wherein the slab has a predetermined height and is configured to deflect a proximal phalanx upwardly relative to a first metatarsal.

In another aspect, the invention relates to a method for improving stability of a foot during ambulation, which includes placing an orthopedic appliance, having a predetermined height, under a big toe such that the slab is located forward of, and does not extend under a head of a first metatarsal of the big toe; and deflecting a proximal phalanx upwardly relative to the first metatarsal.

Other aspects and advantages of the invention will be apparent from the following description and the appended claims.

DETAILED DESCRIPTION

Figure 1:
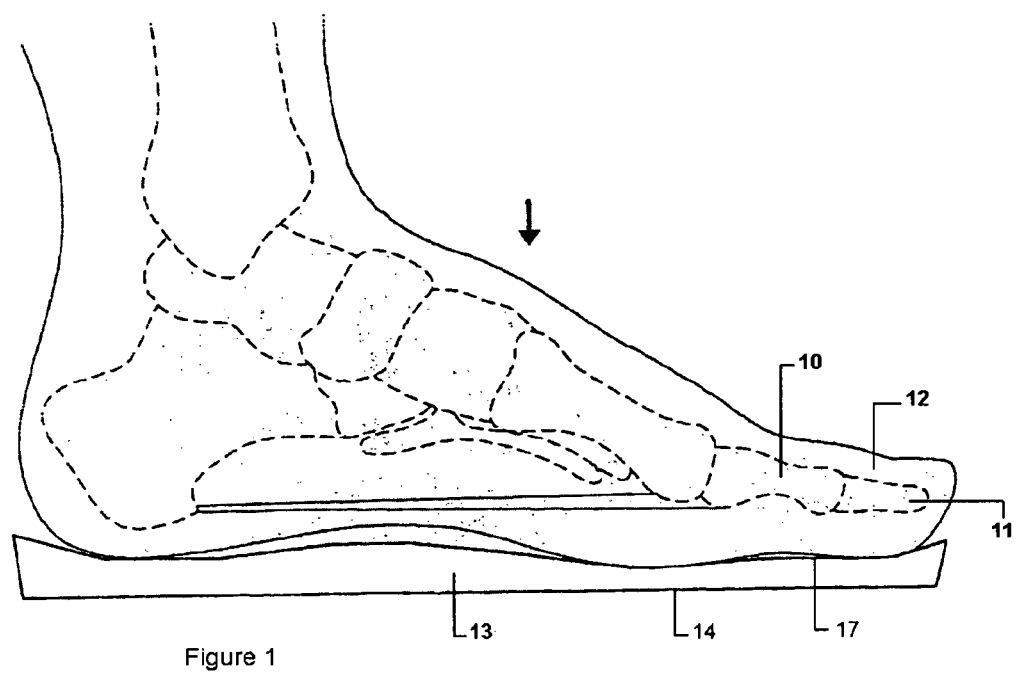
FIG. 1 a prior art figure illustrating the bone structure of a foot on a typical piece of footwear.

First, this invention improves the stability of the foot structure during ambulation. With increased medial column stability of the foot, pain is alleviated in the lesser metatarsal area of the foot. Elevation of the proximal phalanx accomplishes several significant biomechanical sequences which have the effect of providing a supinatory position of the subtalar and midtarsal joints as well as pronation of the longitudinal midtarsal joint. As dorsiflexion of the toes takes place in late midstance and early propulsion, the plantar fascia is placed on stretch. As this occurs, the arch height is increased or the distance between the heel and the ball of the foot is shortened. This results in overall supination of the foot structure which provides for more stability of the foot during stance.

The second advantage to the present invention is alleviation of foot pain caused by limited dorsiflexion of the first metatarsalphlangeal joint. A pronated rearfoot and a supinated forefoot (a flat foot) places the aponeurosis (plantar fascia) under stress. Stress without dorsiflexion of the metatarsalphlangeal joints will result in marked limitation of dorsiflexion of the first metatarsalphlangeal joint causing pain. Use of the present invention prestresses the plantar fascia without limiting the motion of the metatarsalphlangeal joint, alleviating pain caused by stress without dorsiflexion.

The third advantage of the present invention is that it allows for rotation of the hallux around the first metatarsal decreasing the likelihood of degenerative conditions arising over time such as structural hallux rigidus. In normal gait, the first metatarsal hits the surface maximally dorsiflexed. After relaxation of the anterior tibial muscle, the first metatarsal should move towards the weight bearing surface (plantarflex). This is facilitated by rearfoot supination. This plantarflexion is essential for the first metatarsalphlangeal joint to dorsiflex normally in propulsion. The first metatarsalphlangeal joint (big toe joint) must dorsiflex before plantarflexion of the first metatarsal takes place. By placing the proximal phalanx in a dorsiflexed position, as this invention does, the first metatarsal is plantarflexed such that excessive dorsiflexion of the first metatarsal cannot occur with weight bearing reactive forces. The net effect of this is to pronate the longitudinal midtarsal joint axis.

In an abnormal gait without proper foot function, the metatarsal elevates and the first metatarsalphlangeal joint axis is also elevated. Such elevation limits the ability of the hallux to rotate around the elevated first metatarsal segment and is termed functional hallux limitus. When functional hallux limitus occurs over a prolonged period of time, a degenerative joint disease called hallux rigidus may develop. Elevation of the first metatarsal can occur whenever a person over pronates or bears too much weight through the medial (inside) column of the foot. Over pronation is a common biomechanical error in terminal stance and shoe designers for years have been attempting to control abnormal degrees of this motion. By using the present invention, the motion of the hallux is improved in the user, limiting further development of functional hallux limitus and hallux rigidus.

The fourth advantage of this invention is ease of application. The invention may be disposed beneath the hallux in various ways, including formation as part of the sole of footwear, adhesion of the wedge to the inner sole of footwear after manufacture, and adhering the wedge to the hallux for use in the absence of footwear. While manufacture of the present invention can be accomplished in a large scale production, the present invention may also be manufactured in a doctor's office such that they may be custom fit to the individual wearer.

The fifth advantage of this invention is increased angulation of the proximal phalanx in enclosed toe footwear. The angle of inclination in enclosed footwear may be limited by the toe box of footwear. When a straight wedge is placed in an enclosed space, there is a limit to the amount of inclination that may be achieved before the toe strikes the top of the shoe material. By placing the distal phalanx parallel to the bottom surface, or at an angle of declination, greater inclination may be placed under the proximal phalanx. In doing so, more tension is placed on the proximal phalanx, therefore engaging the windlass mechanism. Increased tension increases the corrective forces of the windlass mechanism on the first ray, midtarsal, and subtalar joints.

The sixth advantage of this invention is a more normal position of the foot during ambulation. By placing the distal phalanx parallel to the bottom surface or at an angle of declination in relation to the bottom surface, less tension is put on the flexor hallucis longus tendon. Reducing tension lessens the likelihood of irritation of the tendon on the arch of the insole. Reduced tension also allows for flexion of the distal phalanx which is a normal motion of the foot during late midstance, and is therefore more anatomical.

The seventh advantage of this invention is to correct an element of abnormal motion of the foot which is manifested in the hallux (big toe). As the foot pronates and the LMTJ axis supinates, the hallux will go into a valgus alignment. By placing a slight varus component into the invention, the invention becomes more effective at correcting the abnormal alignment of the hallux (big toe).

When this functional position has been a long standing problem, the valgus alignment becomes fixed and is non-reducible. In this situation, the invention will be more comfortable with a valgus alignment added and allows for the invention to be properly and comfortably used by those with the deformity commonly referred to as hallux valgus.

The eighth advantage of this invention is comfort for the second toe. The invention when used with a non-contoured edge may cause irritation of the second toe in some patients. Therefore by contouring the lateral edge of the invention, in the vertical plane, the second toe will not be in a position to rub on the invention and thus eliminates a possible source of irritation.

FIG. 1 shows a typical view of the foot at rest on a typical shoe insole 13. The hallux 12, composed of the proximal phalanx 10 and distal phalanx 11, is resting on an upper planar surface 17 of the insole 13 that is parallel to a lower planar surface 14 of the insole 13. Without supporting the hallux, there is increased likelihood that there will be excessive mobility of the medial arch area of the foot.

Figure 2:
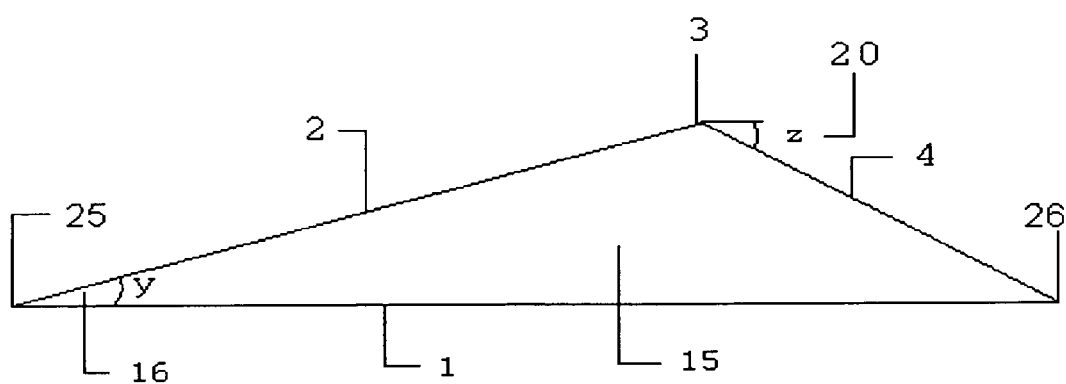
FIG. 2 is a sagittal plane view of one embodiment of the present invention with a severely declining second top surface.

FIG. 2 shows a typical embodiment of the present invention. While the description of the following embodiment recites specific structures such as a wedge, any similar structure may be used. Alternatively, the wedge may also be omitted. The embodiments disclosed herein are for illustrative purposes only and the scope of the invention should not be limited in any way except by the attached claims. The orthopedic apparatus comprises a wedge 15 that has an first upper planar surface 2 disposed between a first end 25, and an apex 3, a second upper planar surface 4, extending from the apex 3 to a second end 26. The first upper planar surface 2 is separated from a lower planar surface 1 by an angle y 16. The angle y 16 is preferably in a range approximately between 1 to 60 degrees, and more preferably between approximately 1 and 20 degrees, for normal ambulation. The angle y 16 can be either increased or decreased depending on the amount of correction desired and the heel height of the shoe. Increased footwear heel height places the hallux at an increased angle of flexion, thus reducing the angle y 16 needed for proper stability. The second upper planar surface 4 is severely declining at an angle z 20 from the apex 3 to the second end 26. In this example, angle z 20 is in a range greater than angle y 16. The wedge 15 may be made of any suitable material commonly employed for such purposes such as flexible material, leather, resilient foam-like material, cork, thermoplastic, or various combinations of materials. The wedge 15 provides a means to elevate the hallux up from the insole and thus up from the floor. The overall length and width of the wedge 15 can vary depending on the individual hallux to be elevated. The wedge 15 will function to stabilize the first metatarsal against ground reactive forces and limit displacement of the first metatarsal upward. Thus, the first metatarsal will plantarflex more easily through the late midstance and propulsive phases of gait. By placing the plantar aponeurosis on stretch there will result a retrograde effect at stabilizing the joints more proximally referred to as the midtarsal joint and the subtalar joint with improved joint congruity and alignment of the foot in relationship to the leg during ambulation. When the first metatarsalphlangeal joint is able to dorsiflex, normal plantarflexion of the first metatarsal is possible and the normal mechanics of the gait cycle are not disrupted during ambulation. The wedge 15 provides for such dorsiflexion of the first metatarsalphlangeal joint of the foot. In this embodiment, the wedge 15 may be adhered along the lower planar surface 1 to the upper planar surface of an insole where the hallux normally rests. The wedge 15 also may be adhered to the hallux along the first upper surface 2 and the second upper planar surface 4.

Figure 3:
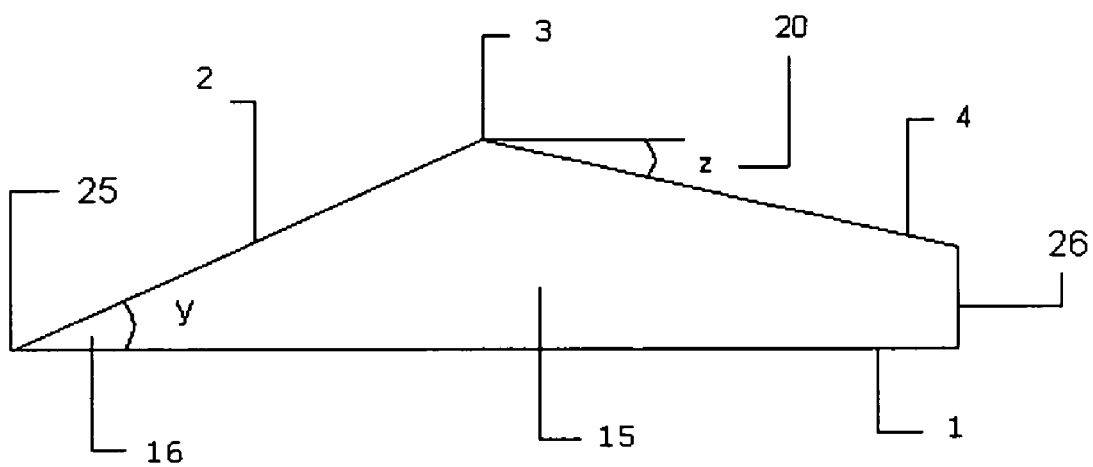
FIG. 3 is a sagittal plane view of one embodiment of the present invention with a slightly declining second top surface.

FIG. 3 shows a sagittal plane view of a typical embodiment of the orthopedic appliance where the wedge 15 that has an first upper planar surface 2 disposed between a first end 25, and an apex 3, a second upper planar surface 4, extending from the apex 3 to a second end 26. The first upper planar surface 2 is separated from a lower planar surface 1 by an angle y 16. The angle y 16 is preferably in a range approximately between 1 to 60 degrees, and more preferably between approximately 1 and 20 degrees, for normal ambulation. The second upper planar surface 4 is mildly declining at an angle z 20 from the apex 3 to the second end 26. Angle z 20 is less than angle y 16. In this embodiment, the wedge 2 may be adhered along the lower planar surface 1 to the upper planar surface of an insole where the hallux normally rests. The wedge 15 also may be adhered to the hallux along the first upper planar surface 2 and the second upper planar surface 4. Adhering the wedge to the hallux along the first upper planar surface 2 and second upper planar surface 4, rather than to the planar surface of footwear where the hallux normally rests, allows the invention to be used in the absence of footwear.

Figure 4:
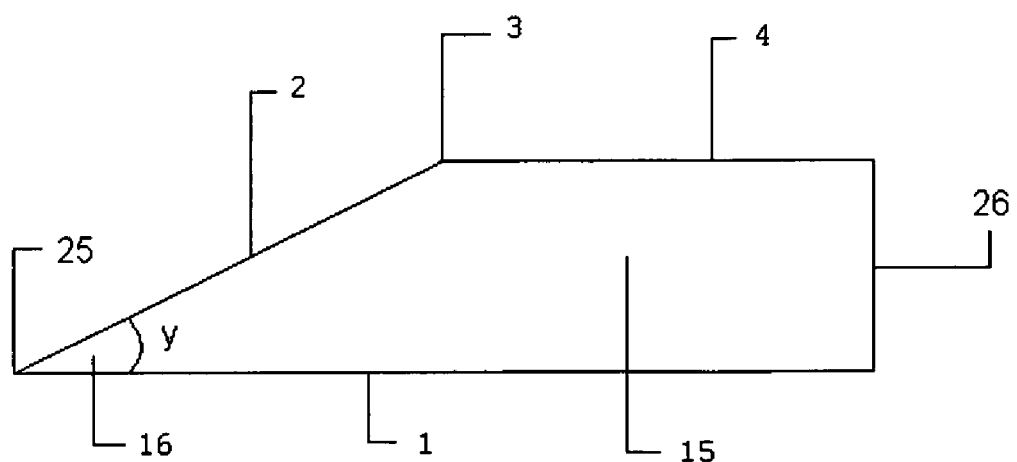
FIG. 4 is a sagittal plane view of one embodiment of the present invention with a second top surface parallel to the bottom surface.

FIG. 4 shows a sagittal plane view of a typical embodiment of the orthopedic appliance where the wedge 15 that has an first upper planar surface 2 disposed between a first end 25, and an apex 3, a second upper planar surface 4, extending from the apex 3 to a second end 26. The first upper planar surface 2 is separated from a lower planar surface 1 by an angle y 16. The angle y 16 is preferably in a range approximately between 1 to 60 degrees, and more preferably between approximately 1 and 20 degrees, for normal ambulation. The second upper planar surface 4 is parallel to the lower planar surface 1 from the apex 3 to the second end 26. In this embodiment, the wedge 15 may be adhered along the lower planar surface 1 to the planar surface of footwear where the hallux normally rests. The wedge 15 also may be adhered to the hallux along the first upper planar surface 2 and the second upper planar surface 4.

Figure 5:
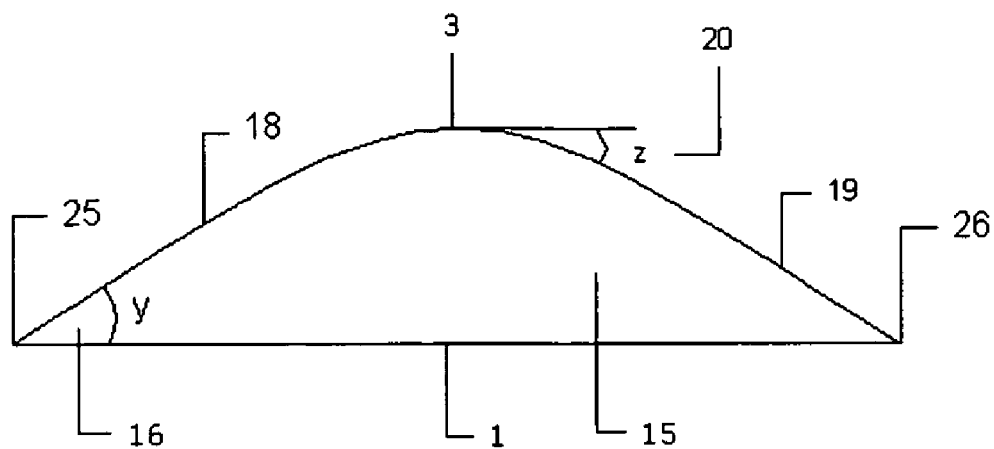
FIG. 5 is a sagittal plane view of one embodiment of the present invention with a severely declining second top surface.

FIG. 5 shows a sagittal plane view of a typical embodiment of the orthopedic appliance comprising a wedge 15 that has an first convex upper surface 18 disposed between a first end 25, and an apex 3, a second convex upper surface 19, extending from the apex 3 to a second end 26. The first convex upper surface 18 is separated from a lower planar surface 1 by an angle y 16. The angle y 16 is preferably in a range approximately between 1 to 60 degrees, and more preferably between approximately 1 and 20 degrees, for normal ambulation. The angle y 16 can be either increased or decreased depending on the amount of correction desired and the heel height of the shoe. Increased footwear heel height places the hallux at an increased angle of flexion, thus reducing the angle y 16 needed for proper stability. The second convex upper surface 19 declines at an angle z 20 from the apex 3 to the second end 26. Angle z 20 is preferably in a range less than angle y 16. The wedge 15 may be made of any suitable material commonly employed for such purposes such as flexible material, leather, resilient foam-like material, cork, thermoplastic, or various combinations of materials. The wedge 15 provides a means to elevate the hallux up from an insole and thus up from the floor. The overall length and width of the wedge 15 can vary dependant on the individual hallux to be elevated. In this embodiment, the wedge 15 may be adhered along the lower planar surface 1 to the upper planar surface of an insole where the hallux normally rests. The wedge 15 also may be adhered to the hallux along the first convex upper surface 18 and the second convex upper surface 19.

Figure 6:
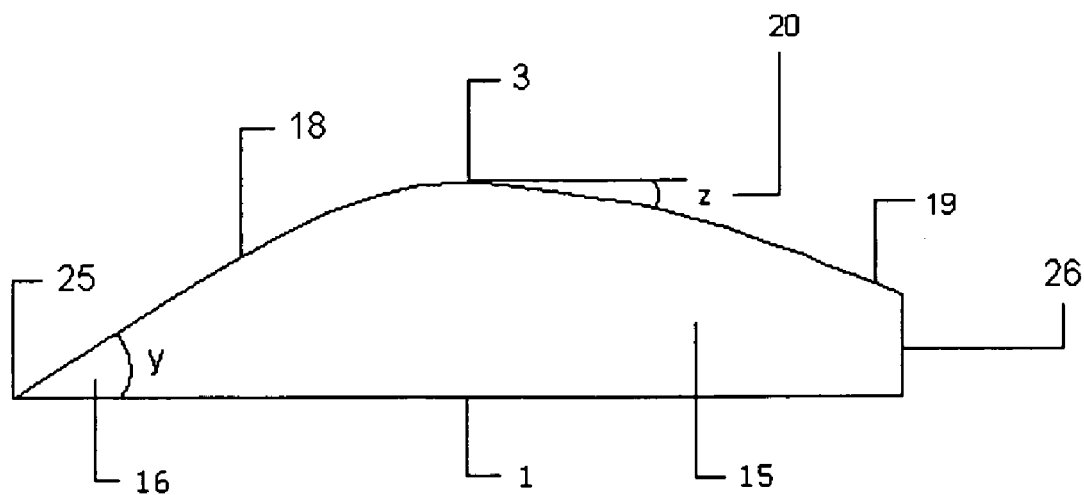
FIG. 6 is a sagittal plane view of one embodiment of the present invention with a slightly declining second top surface.

FIG. 6 shows a sagittal plane view of a typical embodiment of the orthopedic appliance where the wedge 15 that has an first convex upper surface 18 disposed between a first end 25, and an apex 3, a second convex upper surface 19, extending from the apex 3 to a second end 26. The first convex upper surface 18 is separated from a lower planar surface 1 by an angle y 16. The angle y 16 is preferably in a range approximately between 1 to 60 degrees, and more preferably between approximately 1 and 20 degrees, for normal ambulation. The second convex upper surface 19 is mildly declining at an angle z 20 from the apex 3 to the second end 26. Angle z 20 is less than angle y 16. In this embodiment, the wedge 2 may be adhered along the lower planar surface 1 to the upper planar surface of an insole where the hallux normally rests. The wedge 15 also may be adhered to the hallux along the first convex upper surface 18 and the second convex upper surface 19. Adhering the wedge to the hallux along the first convex upper surface 18 and second convex upper surface 19, rather than to the planar surface of footwear where the hallux normally rests, allows the invention to be used in the absence of footwear.

Figure 7:
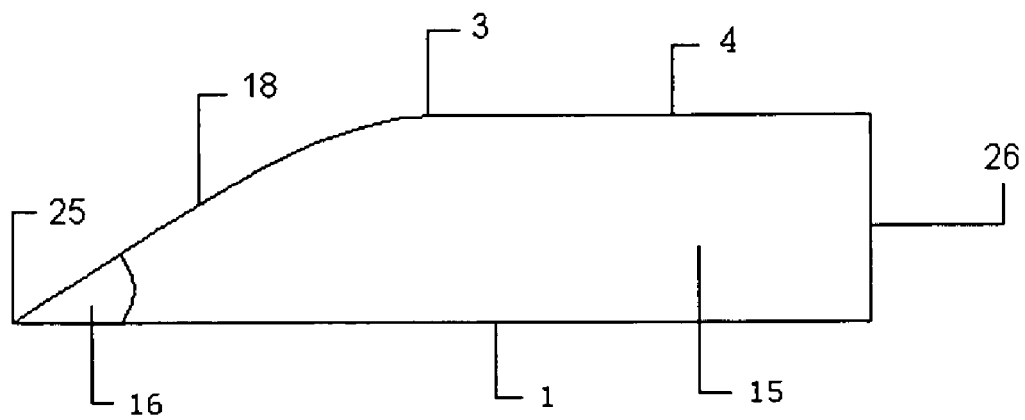
FIG. 7 is a sagittal plane view of one embodiment of the present invention with a second top surface parallel to the bottom surface.

FIG. 7 shows a sagittal plane view of a typical embodiment of the orthopedic appliance where the wedge 15 that has an first convex upper surface 18 disposed between a first end 25, and an apex 3, a second upper planar surface 4 extending from the apex 3 to a second end 26. The first convex upper surface 18 is separated from a lower planar surface 1 by an angle y 16. The angle y 16 is preferably in a range approximately between 1 to 60 degrees, and more preferably between approximately 1 and 20 degrees, for normal ambulation. The second upper planar surface 4 is parallel to the lower planar surface 1 from the apex 3 to the second end 26. In this embodiment, the wedge 15 may be adhered along the lower planar surface 1 to the planar surface of footwear where the hallux normally rests. The wedge 15 also may be adhered to the hallux along the first convex upper surface 18 and the second upper planar surface 4.

Figure 8:
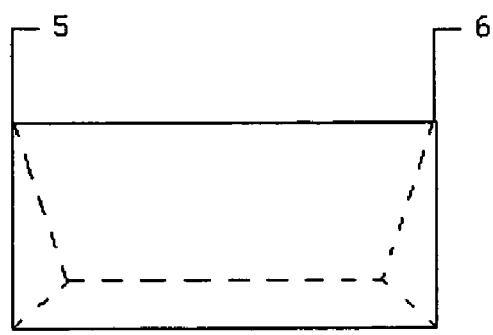
FIG. 8 is a cross section view of one embodiment of the present invention with no lateral to medial slant.

FIG. 8 is a cross section view of the orthopedic appliance shown in FIGS. 2-7 with no grade between a lateral edge 5 and a medial edge 6.

Figure 9:
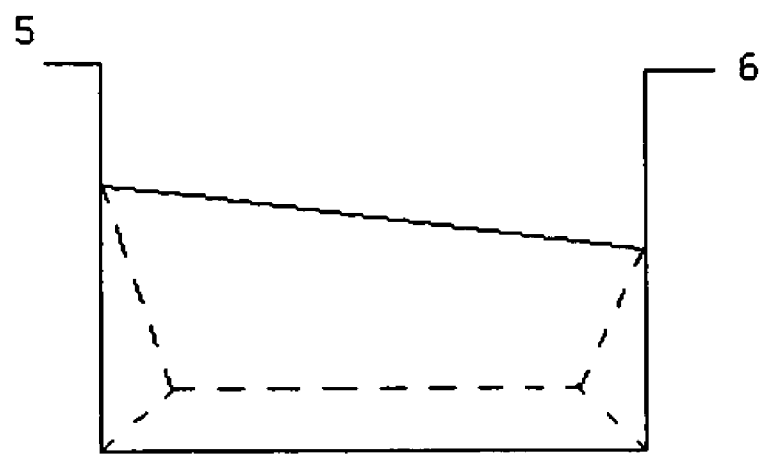
FIG. 9 is a cross section view of one embodiment of the present invention with a lateral to medial slant.

FIG. 9 shows a cross section view of the orthopedic appliance shown in FIGS. 2-7 with the addition of a lateral edge 5 to medial edge 6 grade. The grade decreasing from the lateral edge 5 to the medial edge 6 serves to correct improper valgus alignment of the hallux in relation to the floor. When the foot pronates, the hallux goes into a valgus alignment. By wedging the hallux into a varus alignment, the abnormal valgus alignment is corrected and normal function of the first ray is promoted. Normal function of the first ray will in turn promote normal midtarsal and subtalar joint motion.

Figure 10:
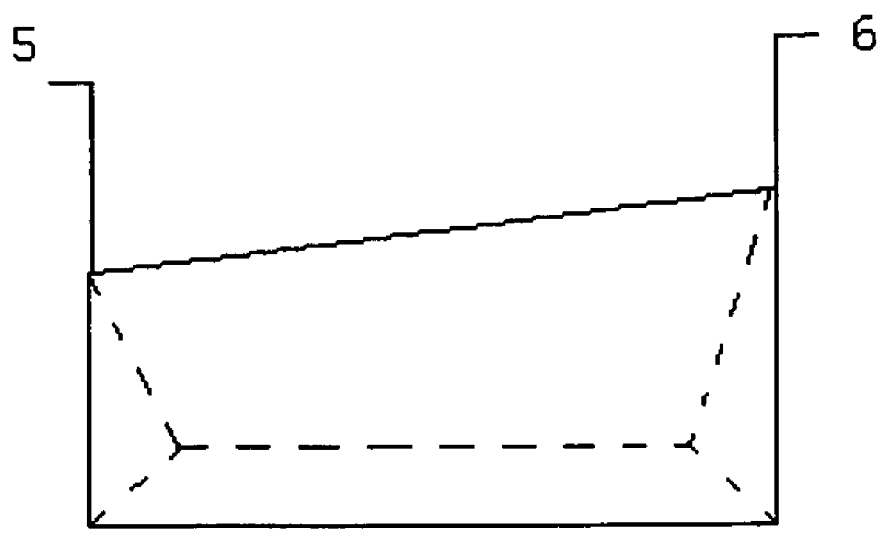
FIG. 10 is a cross section view of one embodiment of the present invention with a medial to lateral slant.

FIG. 10 shows a cross section view of the orthopedic appliance shown in FIGS. 2-7 with the addition of a medial edge 6 to lateral edge 5 grade. With deformity of the first metatarsal phalangeal joint and development of a bunion deformity, the hallux deviates into an abnormal valgus alignment. Initially, this deformity is reversible. However, over time the deformity becomes fixed and non-reducible. In order to accommodate for valgus alignment in patients who could benefit from this invention, a medial to lateral grade is necessary.

Figure 11:
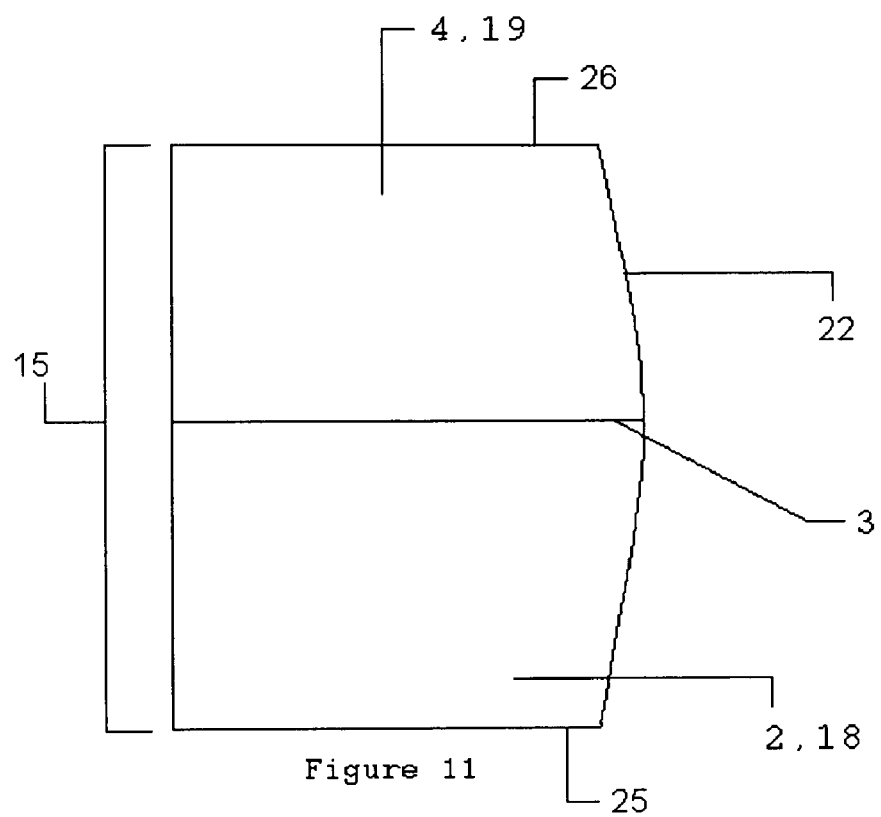
FIG. 11 is a transverse plane view of one embodiment of the present invention straight lateral edge and a convexly contoured medial edge.

FIG. 11 is a perspective view of the embodiment of the orthopedic appliance as shown in FIGS. 2-7 with the addition of a convex medial edge 22.

Figure 12:
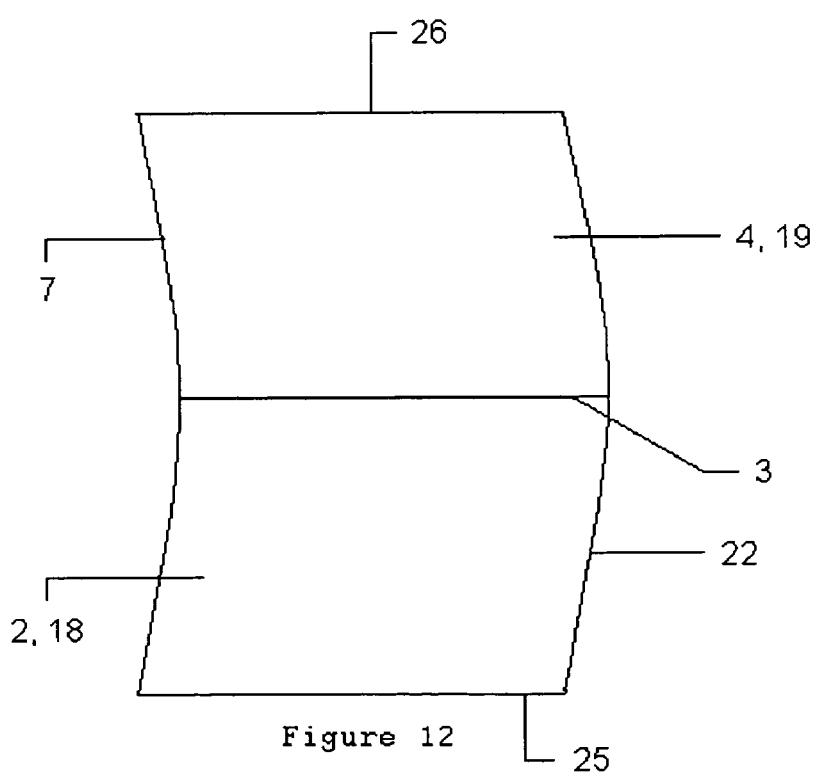
FIG. 12 is a transverse plane view of one embodiment of the present invention with a concavely contoured lateral edge and a convexly contoured medial edge.

FIG. 12 is a perspective view of the embodiment of the orthopedic appliance as shown in FIG. 11 with the addition of a concave lateral edge 7.

Figure 13:
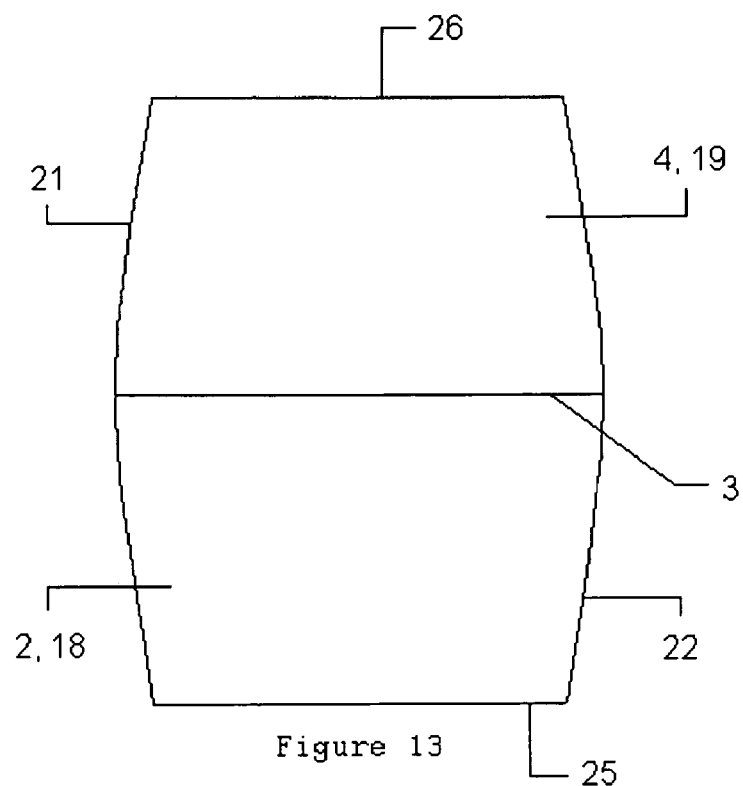
FIG. 13 is a transverse plane view of one embodiment of the present invention with a convexly contoured lateral edge and a convexly contoured medial edge.

FIG. 13 is a perspective view of the embodiment of the orthopedic appliance as shown in FIG. 11 with the addition of a convex lateral edge 21.

Figure 14:
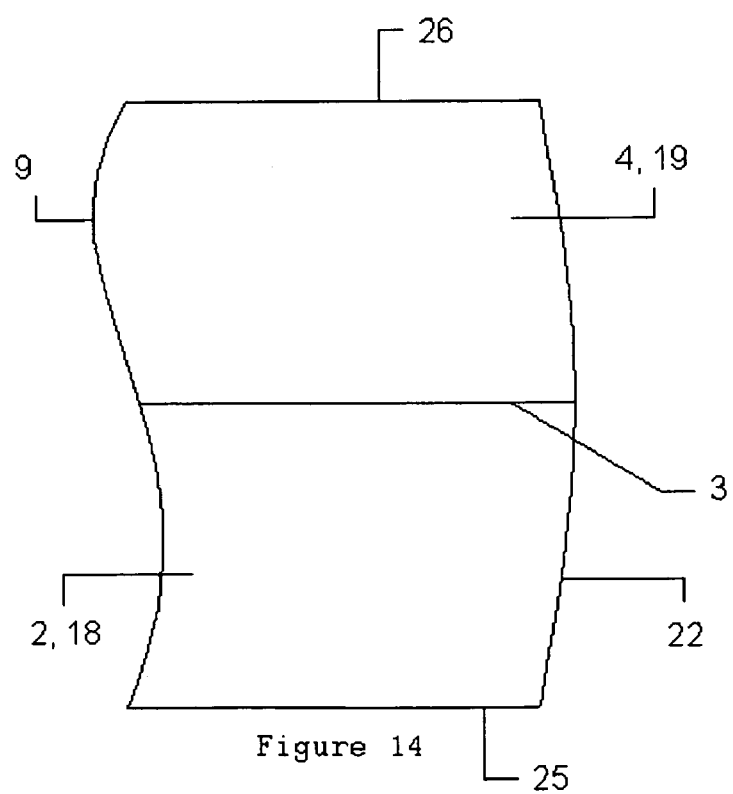
FIG. 14 is a transverse plane view of one embodiment of the present invention with a serpentinely contoured lateral edge and a convexly contoured medial edge.

FIG. 14 is a perspective view of the embodiment of the orthopedic appliance as shown in FIG. 11 with the addition of a serpentine lateral edge 9. The serpentine lateral edge 9 provides for disposing the second toe in the proper orientation and alignment along the serpentine lateral edge 9 of the wedge 15.

Figure 15:
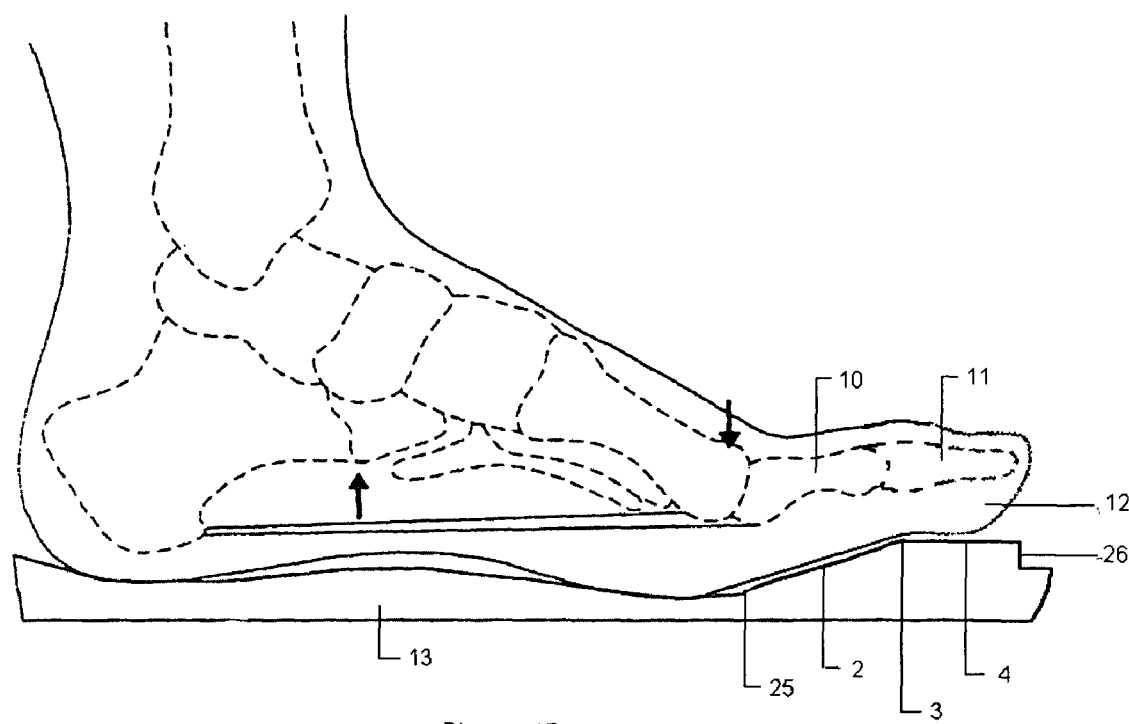
FIG. 15 is a sagittal plane view of the bone structure of the foot illustrating one embodiment of the present invention, formed as a part of the insole footwear, elevating the proximal phalanx and descending the distal phalanx mildly.

FIG. 15 shows a perspective view of the orthopedic appliance shown in FIG. 3. The wedge 15 had been formed as part of the insole 13. However, the wedge might also be formed as part of the midsole, or exterior sole of the footwear.

Figure 16:
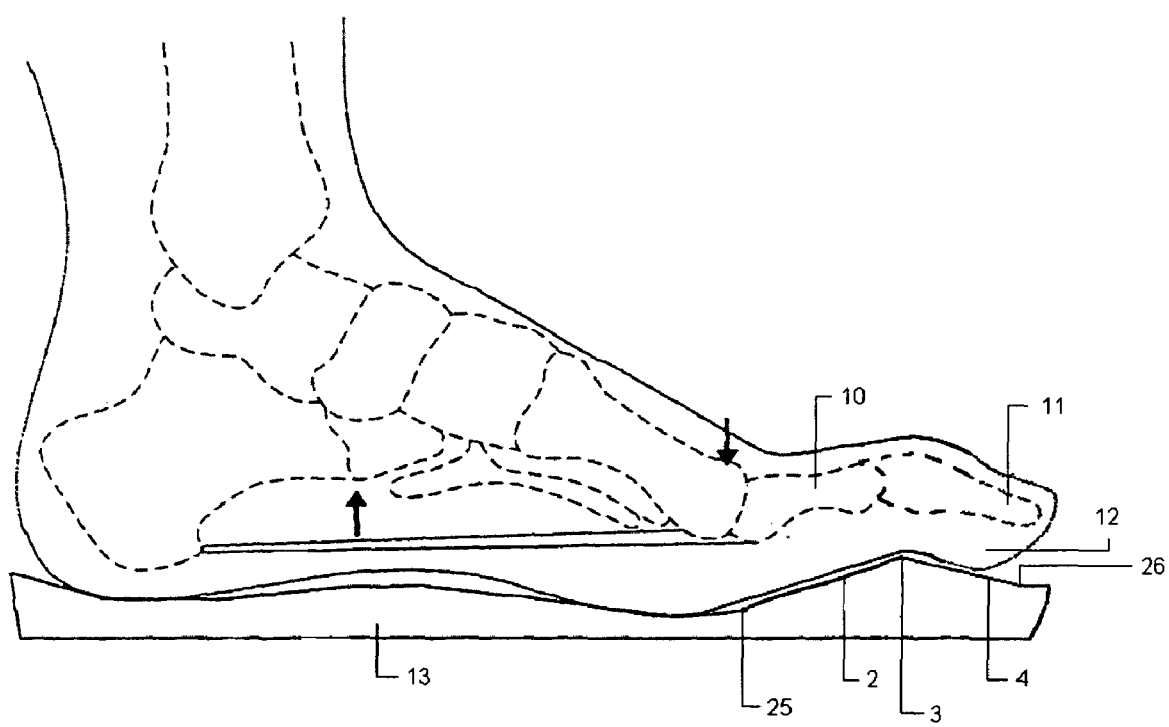
FIG. 16 is a sagittal plane view of the bone structure of the foot illustrating one embodiment of the present invention, formed as a part of the insole footwear, elevating the proximal phalanx and descending the distal phalanx severely.

FIG. 16 shows a perspective view of the orthopedic appliance shown in FIG. 2. The wedge 15 had been formed as part of the insole 13. However, the wedge might also be formed as part of the midsole, or exterior sole of the footwear.

Figure 17:
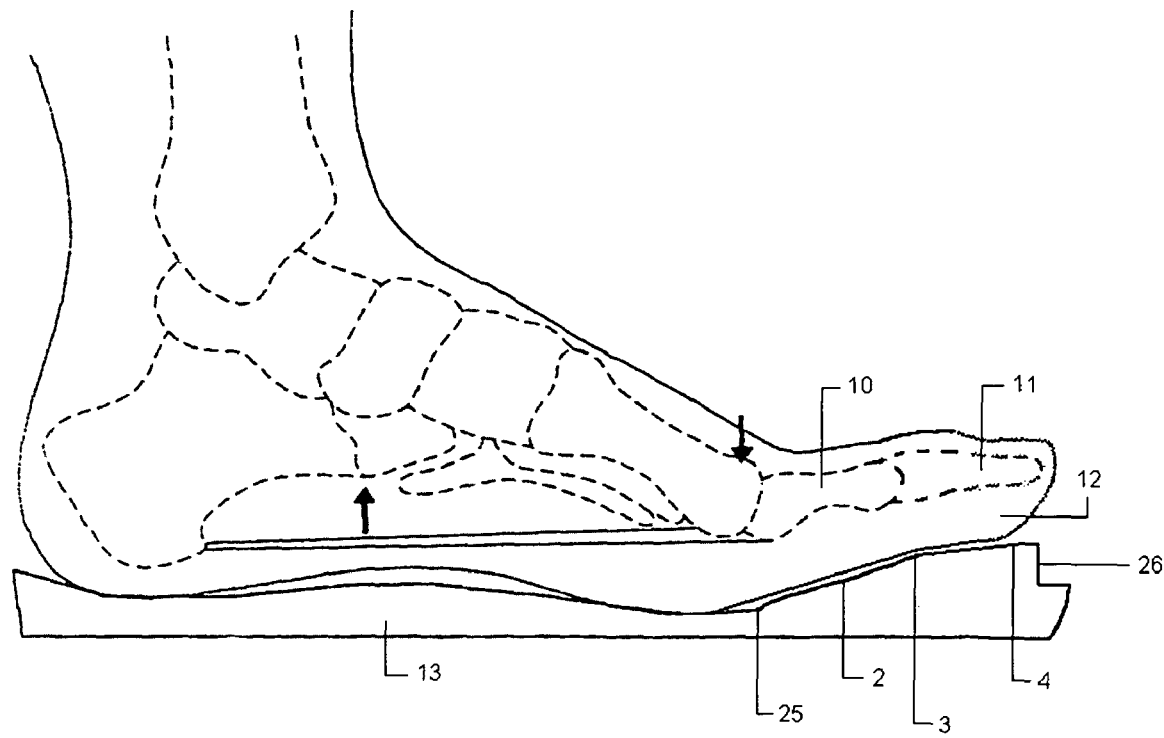
FIG. 17 is a sagittal plane view of the bone structure of the foot illustrating one embodiment of the present invention, formed as a part of the insole footwear, elevating the proximal phalanx and placing the distal phalanx parallel to the bottom surface.

FIG. 17 shows a perspective view of the orthopedic appliance shown in FIG. 4. The wedge 15 had been formed as part of the insole 13. However, the wedge might also be formed as part of the midsole, or exterior sole of the footwear.

Figure 18:
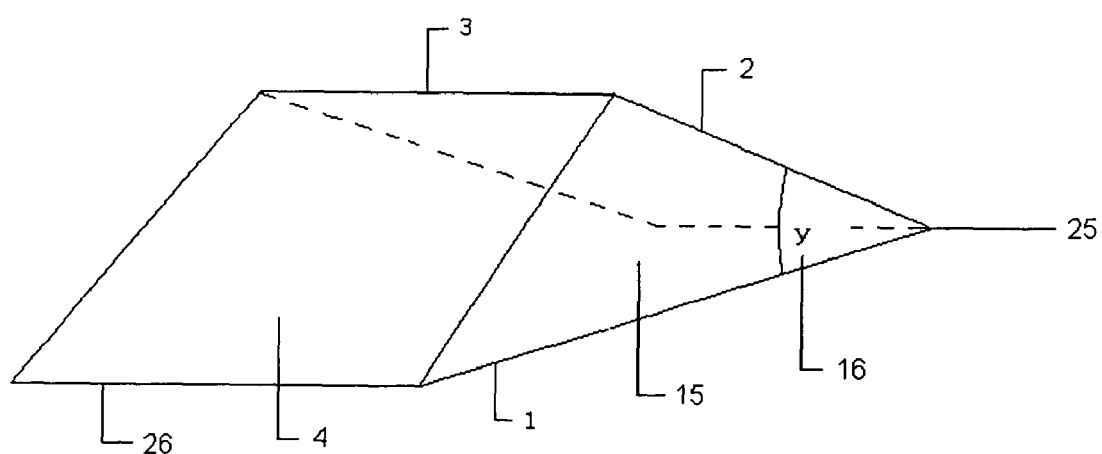
FIG. 18 is a perspective view of FIG. 2.

FIG. 18 shows a perspective view of the orthopedic appliance shown in FIG. 2.

Figure 19:
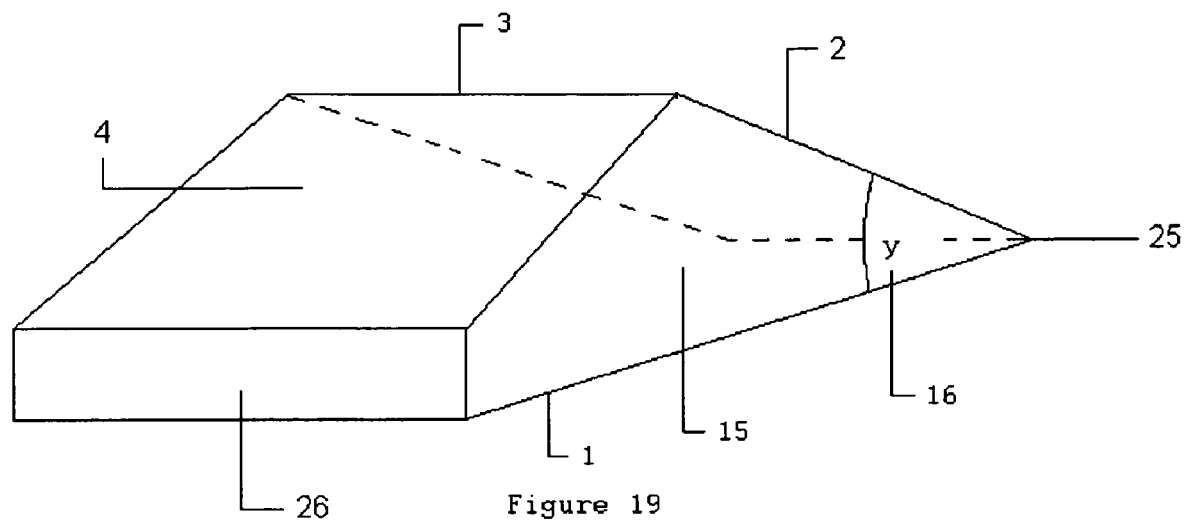
FIG. 19 is a perspective view of FIG. 3.

FIG. 19 shows a perspective view of the orthopedic appliance shown in FIG. 3.

Figure 20:
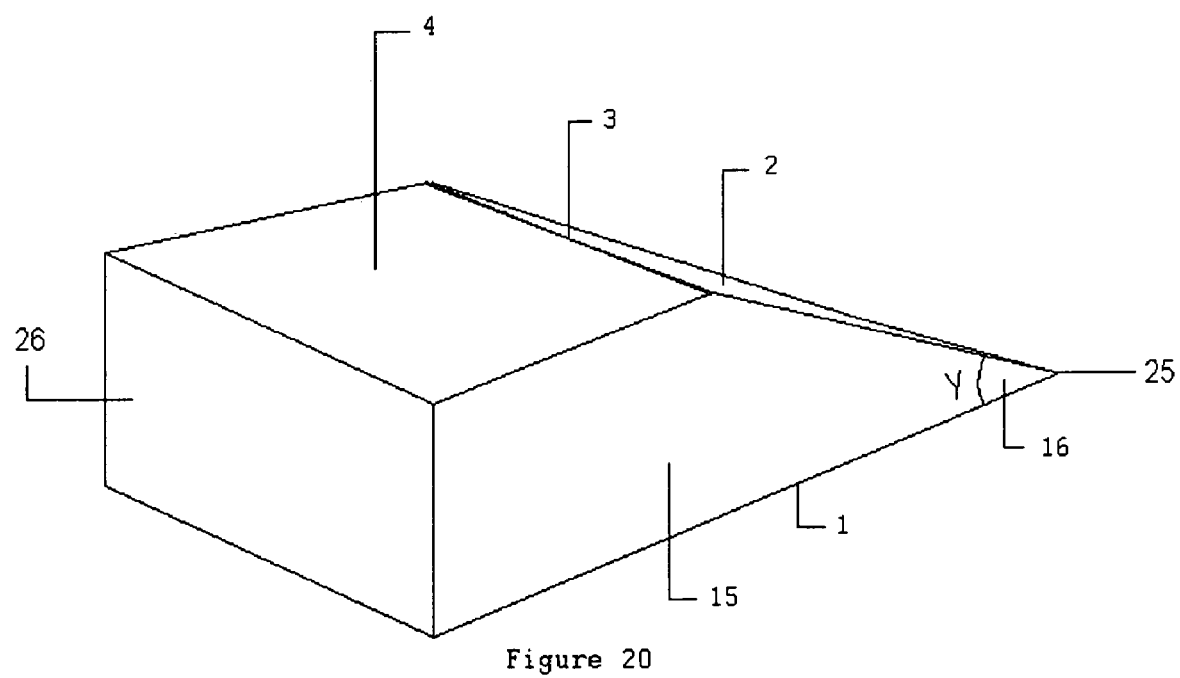
FIG. 20 is a perspective view of FIG. 4.

FIG. 20 shows a perspective view of the orthopedic appliance shown in FIG. 4.

Figure 21:
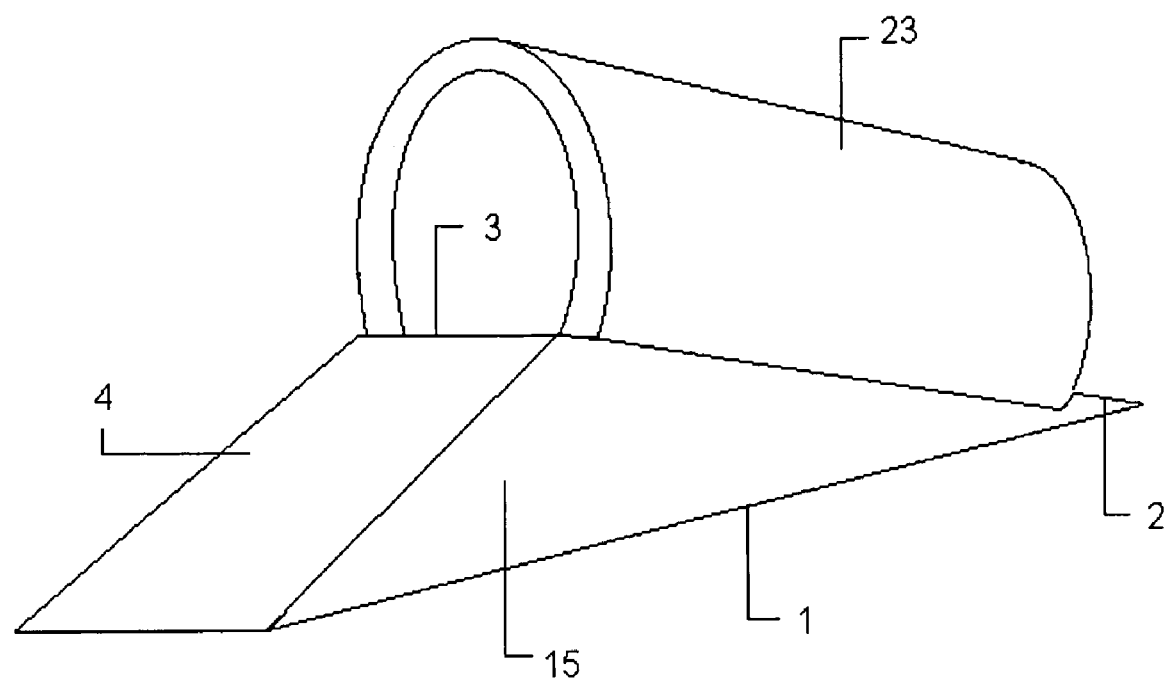
FIG. 21 is a perspective view of FIG. 2 with a single hallux encompassing fastener.

FIG. 21 shows a perspective view of the orthopedic appliance comprising a fastener 23 connected to the wedge 15. The hallux is disposed between the fastener 23, the first upper planar surface 2 and the second upper planar surface 4 in a manner such that the proximal phalanx rests at an increased angle from the lower planar surface 1 of the wedge 15. The fastener 23 creates pressure along the length of the hallux adhering the wedge 15 and the hallux, providing for proper disposition of the wedge 15 beneath the hallux by keeping the hallux in constant contact with the first upper planar surface 2 and the second upper planar surface 4.

Figure 22:
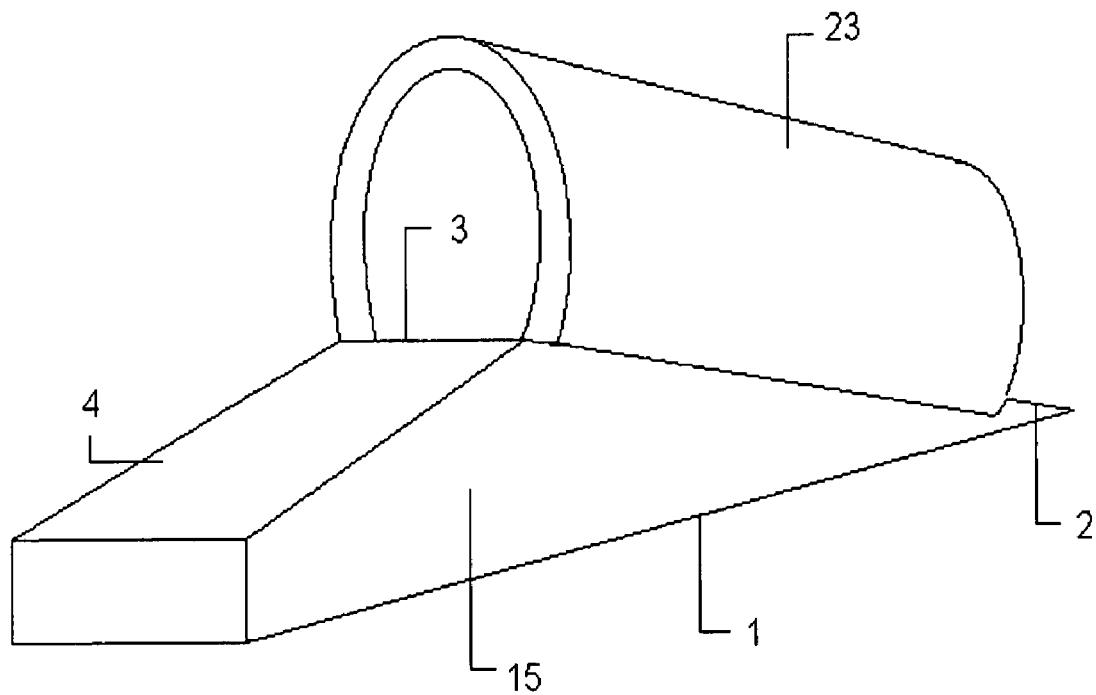
FIG. 22 is a perspective view of FIG. 3 with a single hallux encompassing fastener.

FIG. 22 shows a perspective view of the orthopedic appliance comprising a fastener 23 connected to the wedge 15. The hallux is disposed between the fastener 23, the first upper planar surface 2 and the second upper planar surface 4 in a manner such that the proximal phalanx rests at an increased angle from the lower planar surface 1 of the wedge 15. The fastener 23 creates pressure along the length of the hallux adhering the wedge 15 and the hallux, providing for proper disposition of the wedge 15 beneath the hallux by keeping the hallux in constant contact with the first upper planar surface 2 and the second upper planar surface 4.

Figure 23:
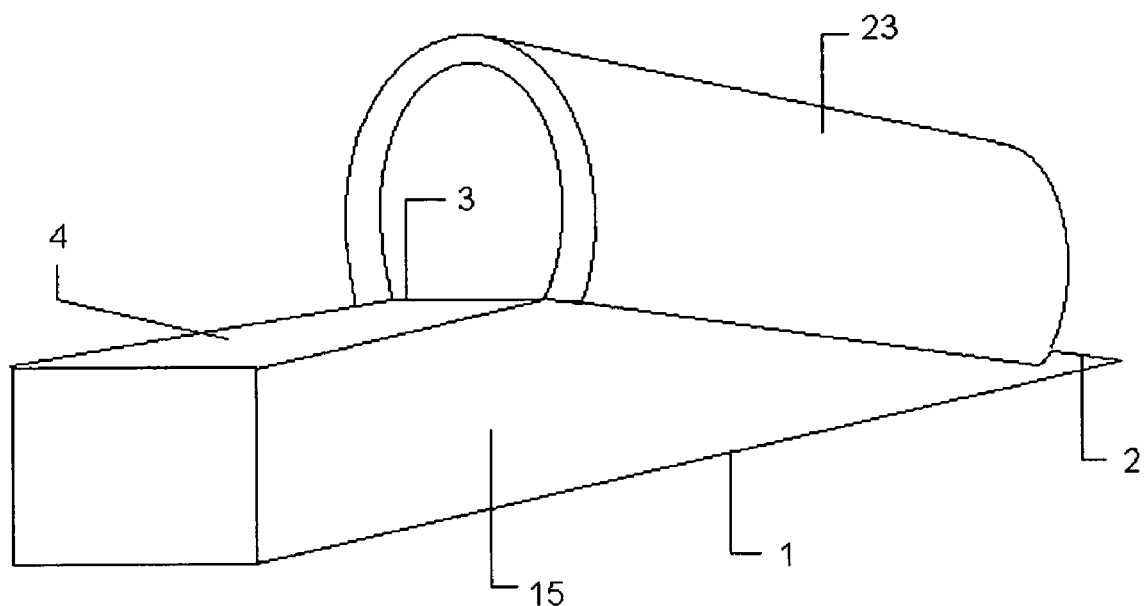
FIG. 23 is a perspective view of FIG. 4 with a single hallux encompassing fastener.

FIG. 23 shows a perspective view of the orthopedic appliance comprising a fastener 23 connected to the wedge 15. The hallux is disposed between the fastener 23, the first upper planar surface 2 and the second upper planar surface 4 in a manner such that the proximal phalanx rests at an increased angle from the lower planar surface 1 of the wedge 15. The fastener 23 creates pressure along the length of the hallux adhering the wedge 15 and the hallux, providing for proper disposition of the wedge 15 beneath the hallux by keeping the hallux in constant contact with the first upper planar surface 2 and the second upper planar surface 4.

Figure 24:
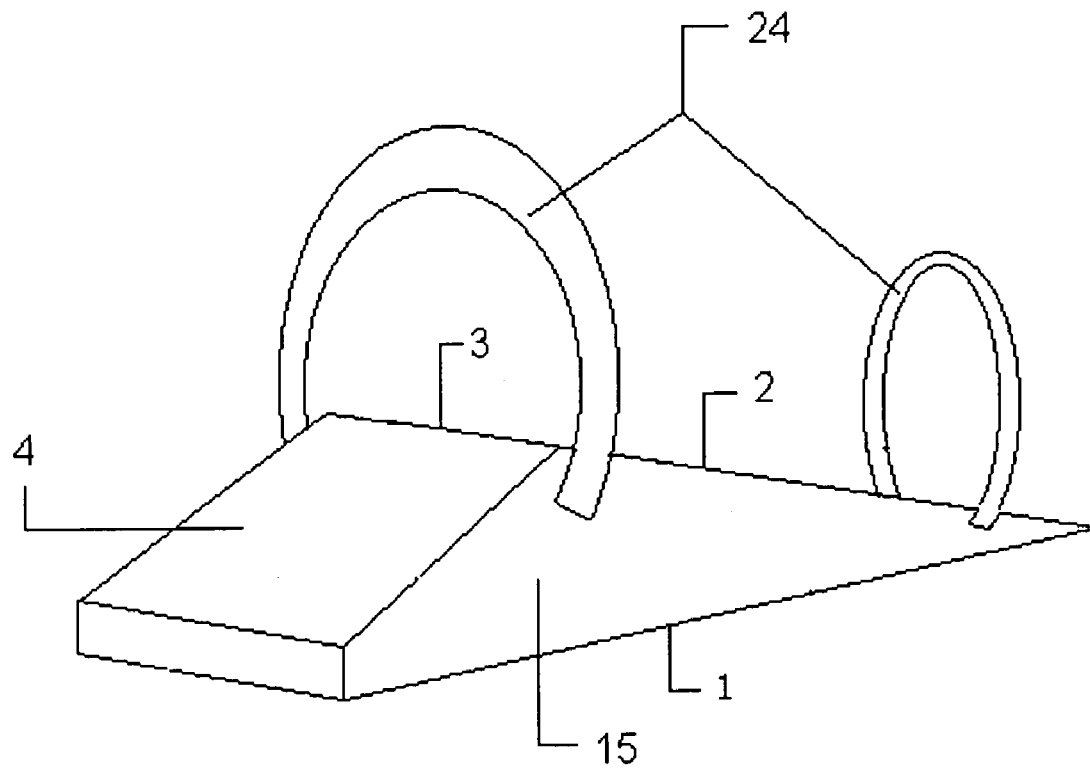
FIG. 24 is a perspective view of one embodiment of the present invention with fasteners.

FIG. 24 shows a perspective view of a typical embodiment of the orthopedic appliance. In this embodiment, the appliance is made up fasteners 24 disposed above the first upper planar surface 2 and second upper planar surface 4 of the wedge 15. The fasteners 24 provide for adhering the wedge 15 to the hallux. The hallux is disposed between the fasteners 24 and the first upper planar surface 2 and second upper planar surface 4 in a manner such that the proximal phalanx rests at an increased angle from the lower planar surface 1 of the wedge 15. The fasteners 24 provide for proper disposition of the wedge 15 beneath the hallux by keeping the hallux in constant contact with the first upper planar surface 2 and second upper planar surface 4 of the wedge 15.

Figure 25:
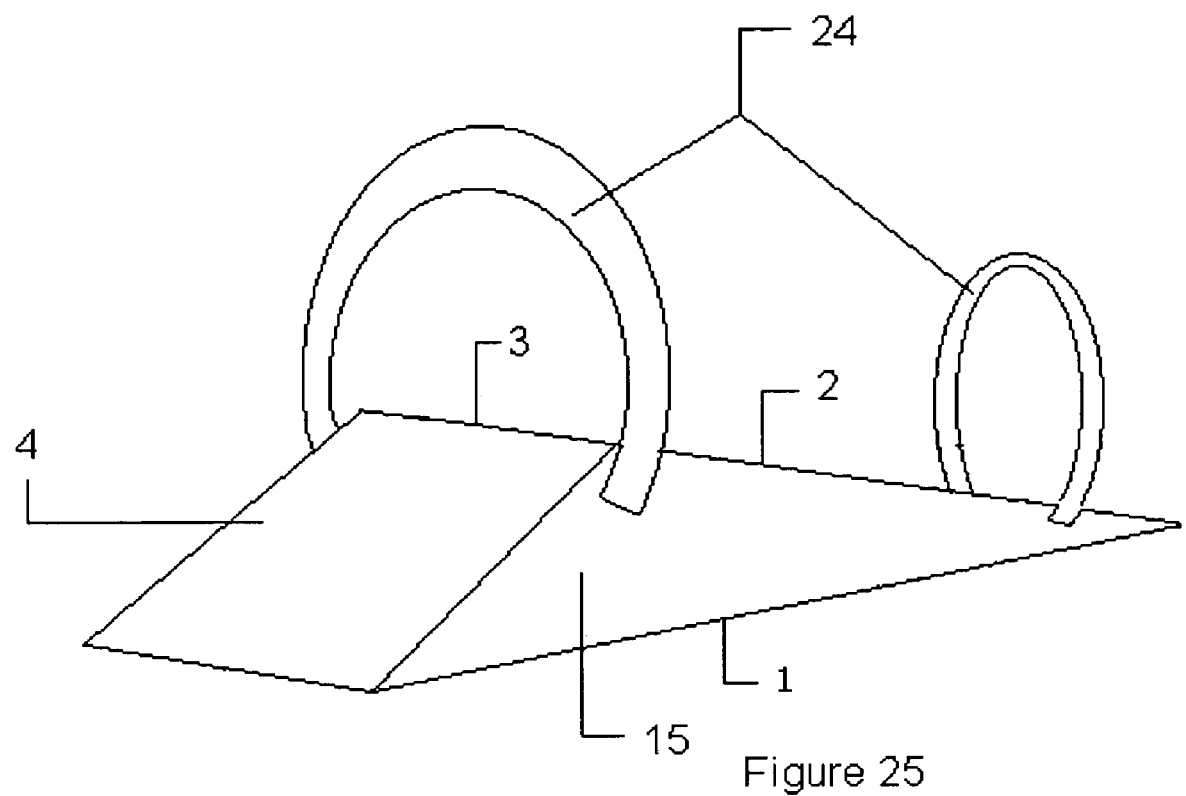
FIG. 25 is a perspective view of one embodiment of the present invention with fasteners.

FIG. 25 shows a perspective view of a typical embodiment of the orthopedic appliance. In this embodiment, the appliance is made up fasteners 24 disposed above the first upper planar surface 2 and second upper planar surface 4 of the wedge 15. The fasteners 24 provide for adhering the wedge 15 to the hallux. The hallux is disposed between the fasteners 24 and the first upper planar surface 2 and second upper planar surface 4 in a manner such that the proximal phalanx rests at an increased angle from the lower planar surface 1 of the wedge 15. The fasteners 24 provide for proper disposition of the wedge 15 beneath the hallux by keeping the hallux in constant contact with the first upper planar surface 2 and second upper planar surface 4 of the wedge 15.

Figure 26:
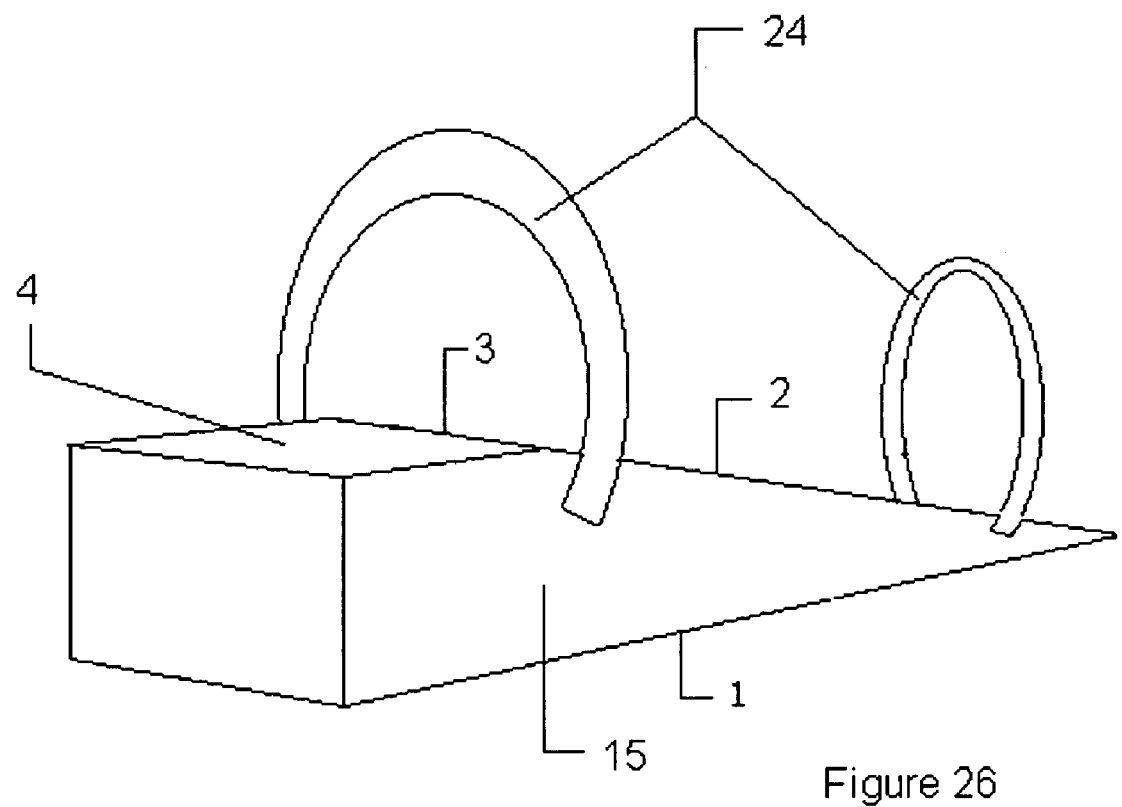
FIG. 26 is a perspective view of one embodiment of the present invention with fasteners.

FIG. 26 shows a perspective view of a typical embodiment of the orthopedic appliance. In this embodiment, the appliance is made up fasteners 24 disposed above the first upper planar surface 2 and second upper planar surface 4 of the wedge 15. The fasteners 24 provide for adhering the wedge 15 to the hallux. The hallux is disposed between the fasteners 24 and the first upper planar surface 2 and second upper planar surface 4 in a manner such that the proximal phalanx rests at an increased angle from the lower planar surface 1 of the wedge 15. The fasteners 24 provide for proper disposition of the wedge 15 beneath the hallux by keeping the hallux in constant contact with the first upper planar surface 2 and second upper planar surface 4 of the wedge 15.

Figure 27:
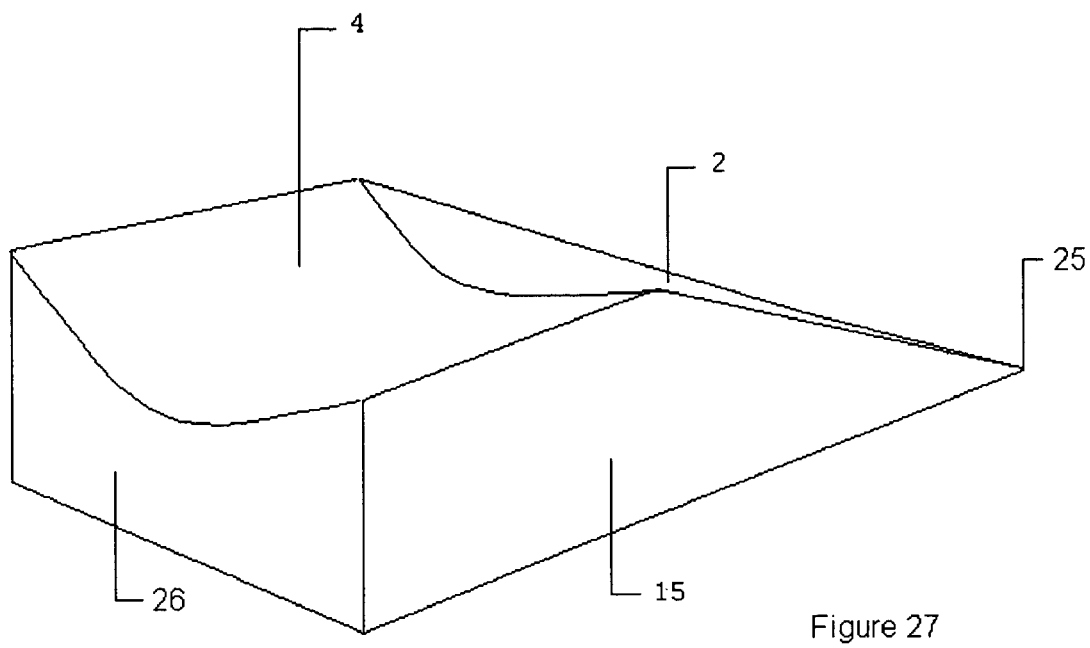
FIG. 27 is a perspective view of one embodiment of the present invention illustrating a concave depression in a first and second top surface.

FIG. 27 shows a perspective view of the orthopedic appliance shown in FIG. 4 with the addition of a concave depression to the wedge 15. In this embodiment, the first upper planar surface 2 and second upper planar surface 4 includes a concave depression disposed along the wedge 15, cradling the hallux, running from the first end 25 to the second end 26. The concave depression provides for disposing the hallux in the proper position along the first upper planar surface 2 and second upper planar surface 4.

Figure 28:
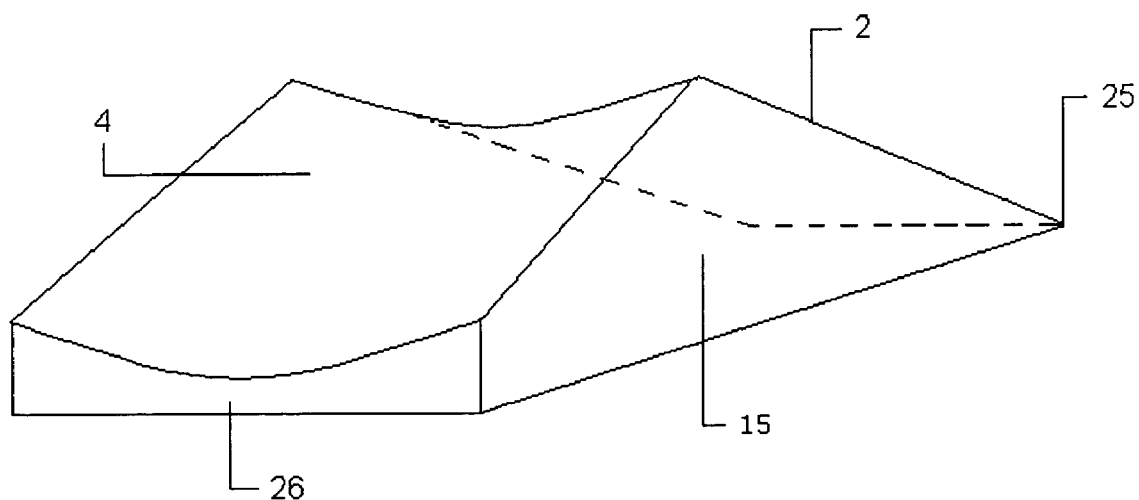
FIG. 28 is a perspective view of one embodiment of the present invention illustrating a concave depression in a first and second top surface.

FIG. 28 shows a perspective view of the orthopedic appliance shown in FIG. 3 with the addition of a concave depression to the wedge 15. In this embodiment, the first upper planar surface 2 and second upper planar surface 4 includes a concave depression disposed along the wedge 15, cradling the hallux, running from first end 25 to the second end 26. The concave depression provides for disposing the hallux in the proper position along the first upper planar surface 2 and second upper planar surface 4.

Figure 29:
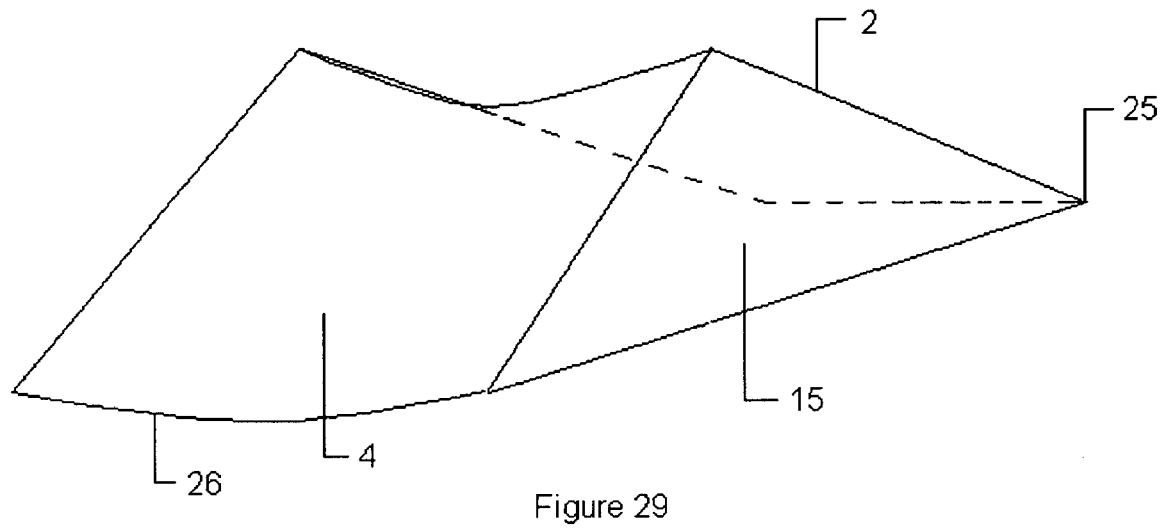
FIG. 29 is a perspective view of one embodiment of the present invention illustrating a concave depression in a first and second top surface.

FIG. 29 shows a perspective view of the orthopedic appliance shown in FIG. 2 with the addition of a concave depression to the wedge 15. In this embodiment, the first upper planar surface 2 and second upper planar surface 4 includes a concave depression disposed along the wedge 15, cradling the hallux, running from first end 25 to the second end 26. The concave depression provides for disposing the hallux in the proper position along the first upper planar surface 2 and second upper planar surface 4.

Figure 30:
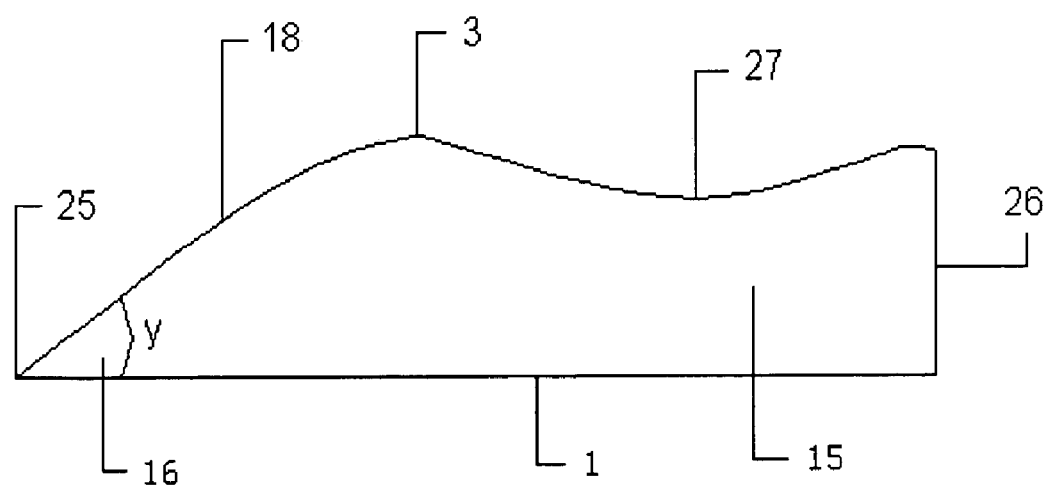
FIG. 30 is a sagittal plane view of one embodiment of the present invention with a first upper convex surface and a second upper concave surface.

FIG. 30 shows a sagittal plane view of a typical embodiment of the orthopedic appliance comprising a wedge 15 that has an first convex upper surface 18 disposed between a first end 25, and an apex 3, a second concave upper surface 27, extending from the apex 3 to a second end 26. The first convex upper surface 18 is separated from a lower planar surface 1 by an angle y 16. The angle y 16 is preferably in a range approximately between 1 to 60 degrees, and more preferably between approximately 1 and 20 degrees, for normal ambulation. The angle y 16 can be either increased or decreased depending on the amount of correction desired and the heel height of the shoe. Increased footwear heel height places the hallux at an increased angle of flexion, thus reducing the angle y 16 needed for proper stability. The wedge 15 may be made of any suitable material commonly employed for such purposes such as flexible material, leather, resilient foam-like material, cork, thermoplastic, or various combinations of materials. The wedge 15 provides a means to elevate the hallux up from the insole 13 and thus up from the floor. The overall length and width of the wedge 15 can vary dependant on the individual hallux 12 to be elevated. In this embodiment, the wedge 15 may be adhered along the lower planar surface 1 to the upper planar surface 17 of the insole 13 where the hallux 12 normally rests. The wedge 15 also may be adhered to the hallux 12 along the first convex upper surface 18 and the second convex upper surface 19.

Figure 31:
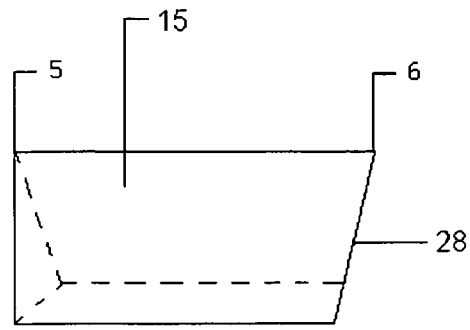
FIG. 31 is a cross section-view of one embodiment of the present invention with an angled lateral edge.

FIG. 31 is a cross section view of the orthopedic appliance shown in FIG. 8 with the addition of an angled grade 28. In this embodiment, the lateral edge 6 includes a angled grade disposed along the length of the wedge 15. The angled grade 28 provides for disposing the second toe in the proper orientation and alignment along the lateral edge 6 of the wedge 15.

Figure 32:
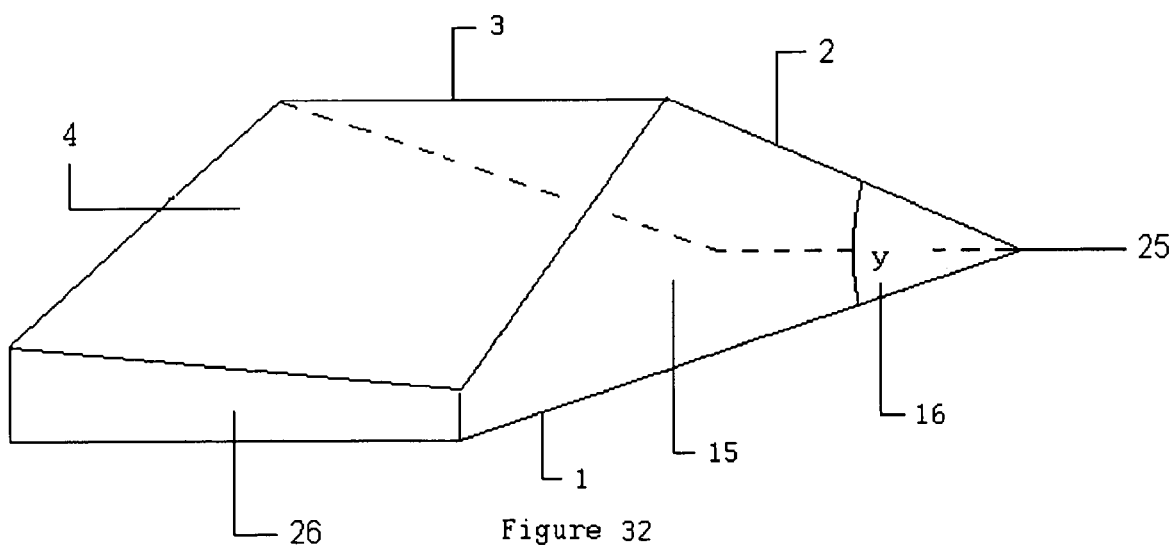
FIG. 32 is as a perspective view of FIG. 3 with a valgus orientation in the second top surface.

FIG. 32 is a perspective view of FIG. 3 with the addition of a valgus orientation (a valgus angled grade) in the second top surface 4 of the wedge 15. In the embodiment, the apex 3 is parallel to the lower planar surface of the wedge 1 and does not have a valgus orientation as does the second top surface 4 and the second end 26. The valgus orientation serves to accommodate improper fixed valgus alignment of the hallux in relation to the lower planar surface of the wedge 1 and the floor.

Figure 33:
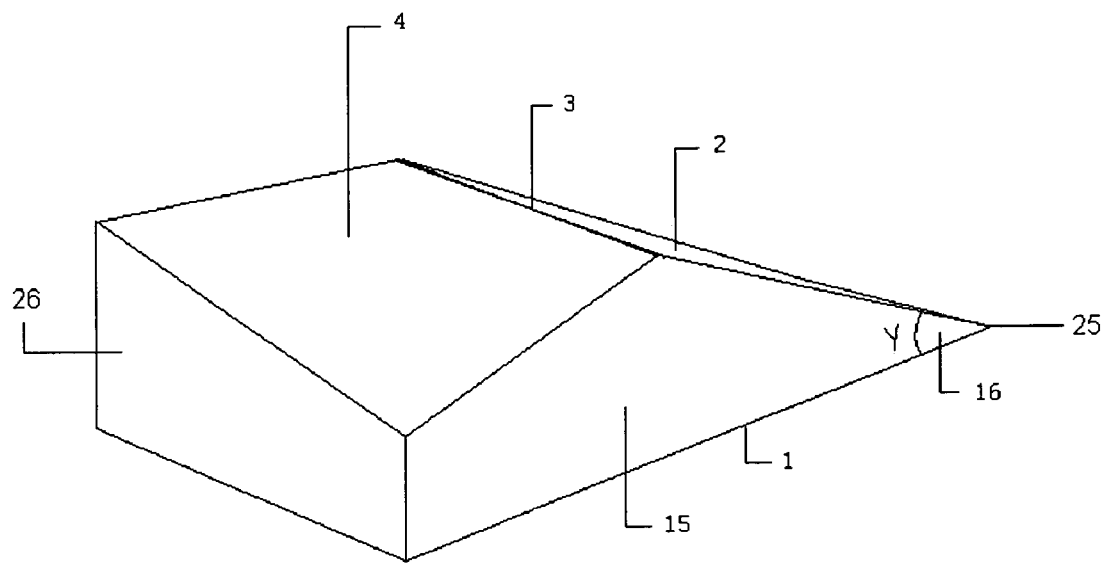
FIG. 33 is a perspective view of FIG. 4 with a valgus orientation in the second top surface.

FIG. 33 is a perspective view of FIG. 4 with the addition of a valgus orientation (a valgus angled grade) in the second top surface 4 of the wedge, 15. In the embodiment, the apex 3 is parallel to the lower planar surface of the wedge 1 and does not have a valgus orientation as does the second top surface 4 and the second end 26. The valgus orientation serves to accommodate improper fixed valgus alignment of the hallux in relation to the lower planar surface of the wedge 1 and the floor.

Figure 34:
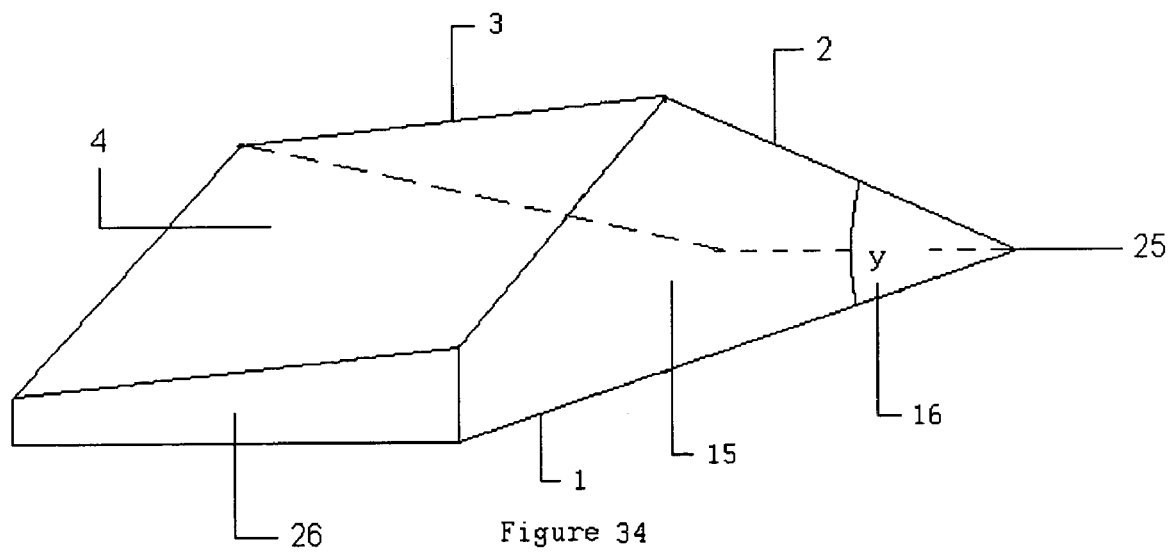
FIG. 34 is a perspective view of FIG. 3 with a varus orientation in the first and second top surfaces.

FIG. 34 is a perspective view of FIG. 3 with the addition of a varus orientation (a varus angled grade) in the first top surface 2 and the second top surface 4 of the wedge 15. Having a varus orientation, the apex 3 is not parallel to the lower planar surface of the wedge 1 and has a varus orientation as does the second top surface 4 and the second end 26. The varus orientation serves to correct improper valgus alignment of the hallux in relation to the lower planar surface of the wedge 1 and the floor. When the foot pronates, the hallux goes into a valgus alignment. By wedging the hallux into a varus alignment, the abnormal valgus alignment is corrected and normal function of the first ray is promoted. Normal function of the first ray will in turn promote normal midtarsal and subtalar joint motion.

Figure 35:
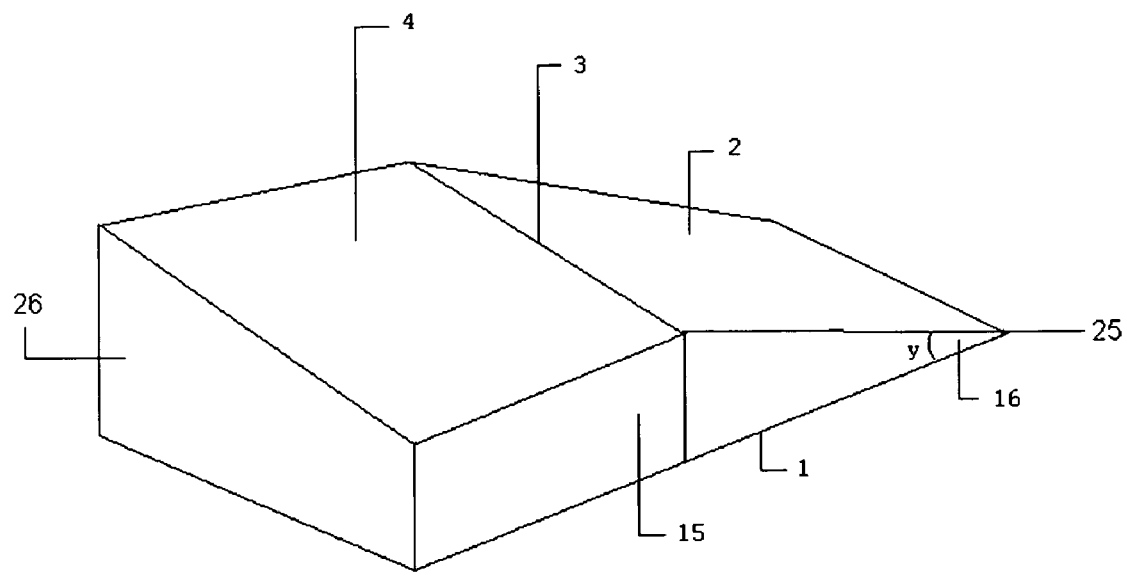
FIG. 35 is a perspective view of FIG. 4 with a valgus orientation in the first and second top surfaces.

FIG. 35 is a perspective view of FIG. 4 with the addition of a valgus orientation (a valgus angled grade) in the second top surface 4 of the wedge 15. In the embodiment, the apex 3 is not parallel to the lower planar surface of the wedge 1 and has a valgus orientation as does the second top surface 4 and the second end 26. The valgus orientation serves to accommodate improper fixed valgus alignment of the hallux in relation to the lower planar surface of the wedge 1 and the floor.

Figure 36:
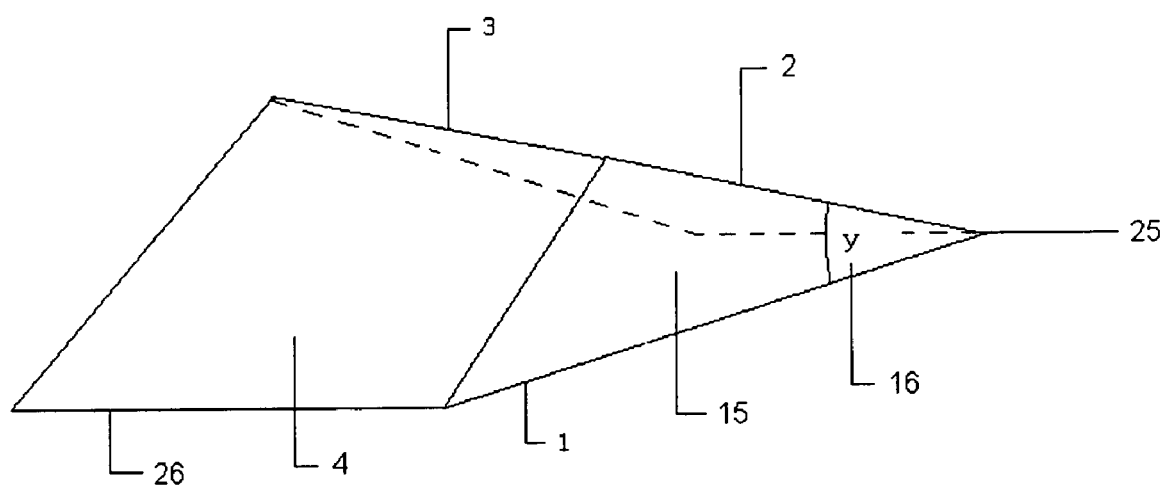
FIG. 36 is a perspective view of FIG. 2 with a valgus orientation in the first and second top surfaces.

FIG. 36 is a perspective view of FIG. 2 with the addition of a valgus orientation (a valgus angled grade) in the second top surface 4 of the wedge 15. In the embodiment, the apex 3 is not parallel to the lower planar surface of the wedge 1 and has a valgus orientation as does the second top surface 4 and the second end 26. The valgus orientation serves to accommodate improper fixed valgus alignment of the hallux in relation to the lower planar surface of the wedge 1 and the floor.

Figure 37:
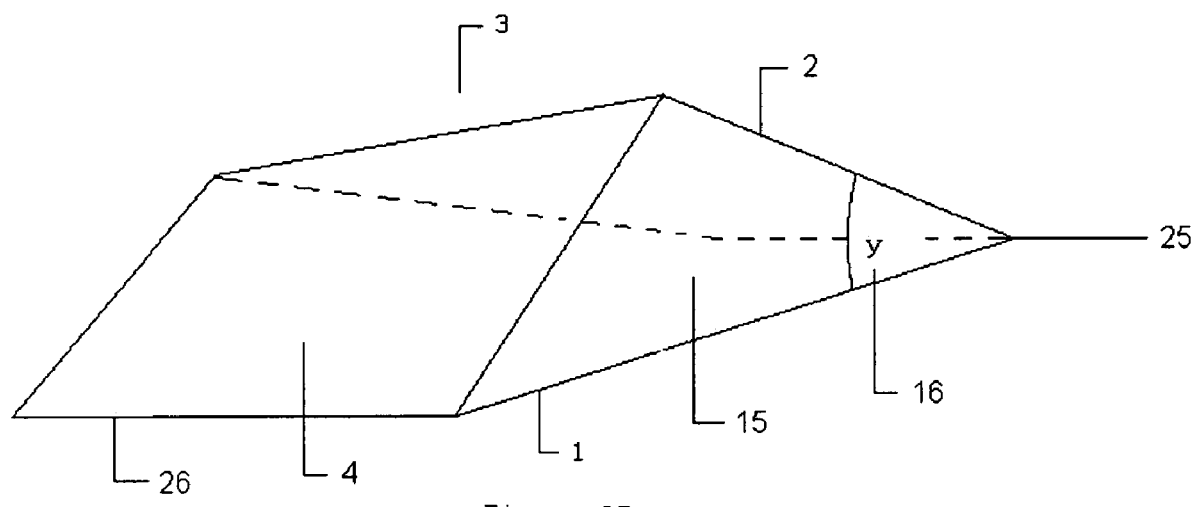
FIG. 37 is a perspective view of FIG. 2 with a varus orientation in the first and second top surfaces.
Figure 38:
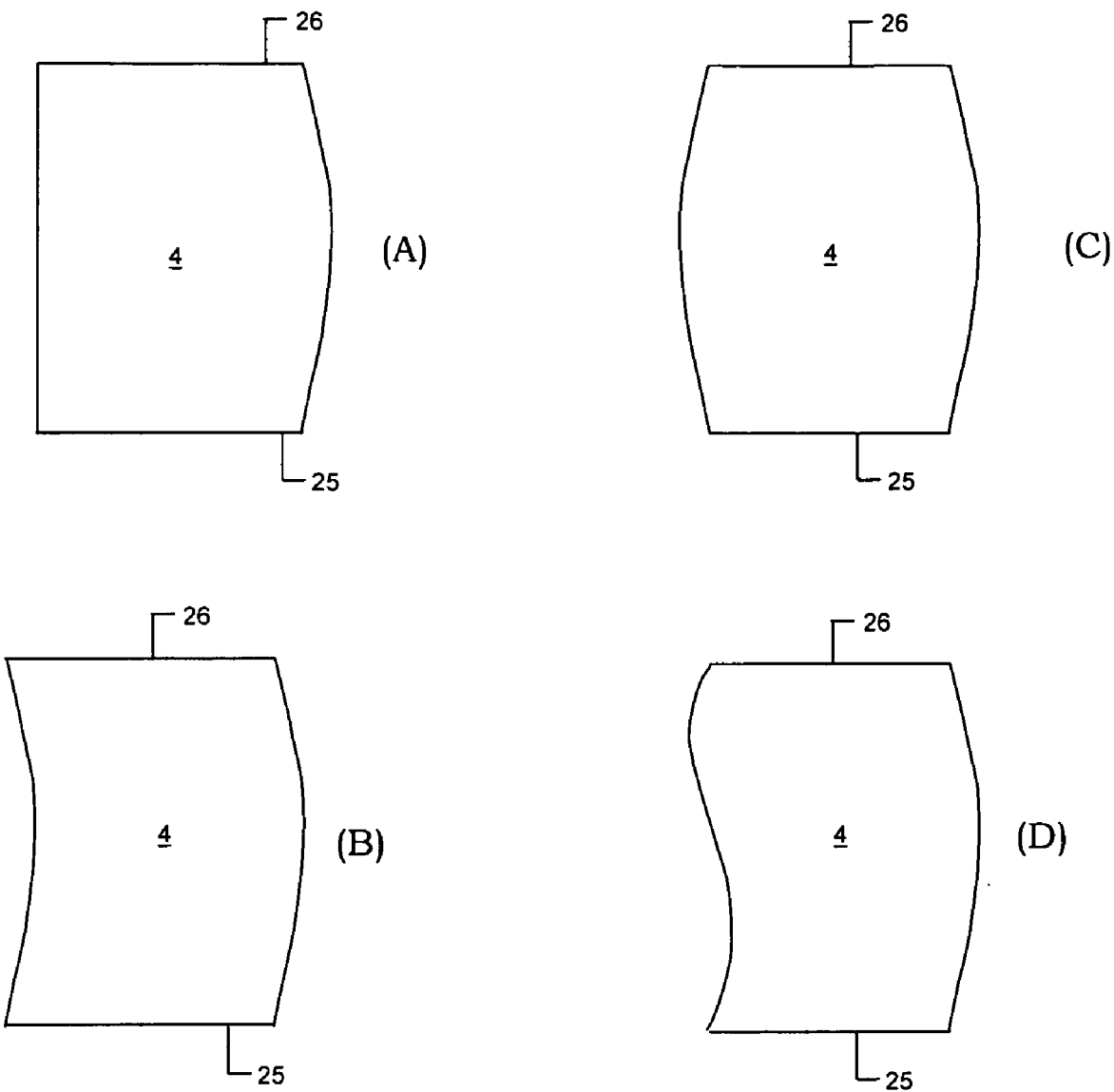
FIGS. 38A-38D show top views of some embodiments of the present invention.

FIG. 37 is a perspective view of FIG. 2 with the addition of a varus orientation (a varus angled grade) in the first top surface 2 and the second top surface 4 of the wedge 15. Having a varus orientation, the apex 3 is not parallel to the lower planar surface of the wedge 1 and has a varus orientation as does the second top surface 4 and the second end 26. The varus orientation serves to correct improper valgus alignment of the hallux in relation to the lower planar surface of the wedge 1 and the floor. When the foot pronates, the hallux goes into a valgus alignment. By wedging the hallux into a varus alignment, the abnormal valgus alignment is corrected and normal function of the first ray is promoted. Normal function of the first ray will in turn promote normal midtarsal and subtalar joint motion.

In accordance with embodiments of the invention, the orthopedic appliances generally comprise slabs, having various shapes to accommodate the shapes of the footwear or to make these appliances more comfortable to wear. FIGS. 38A-38D show the top views of some of these appliances, illustrating different shapes of the upper surfaces 4 disposed between first ends 25, and second ends 26.

Figure 39:
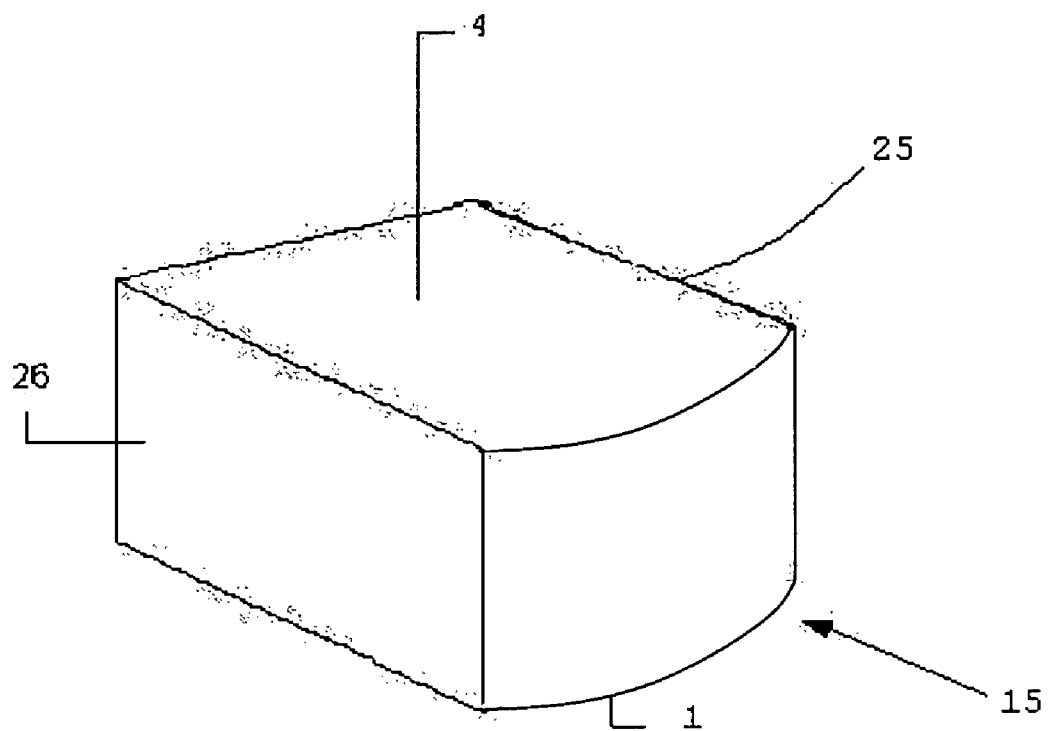
FIG. 39 is a perspective view of FIG. 38A.

In accordance with some embodiments, the upper surfaces 4 may be parallel to the lower surfaces 1, as illustrated in FIG. 39. FIG. 39 shows a perspective view of the embodiment shown in FIG. 38A, illustrating that the top surface 4 is planar and parallel to the bottom surface 1.

Figure 40:
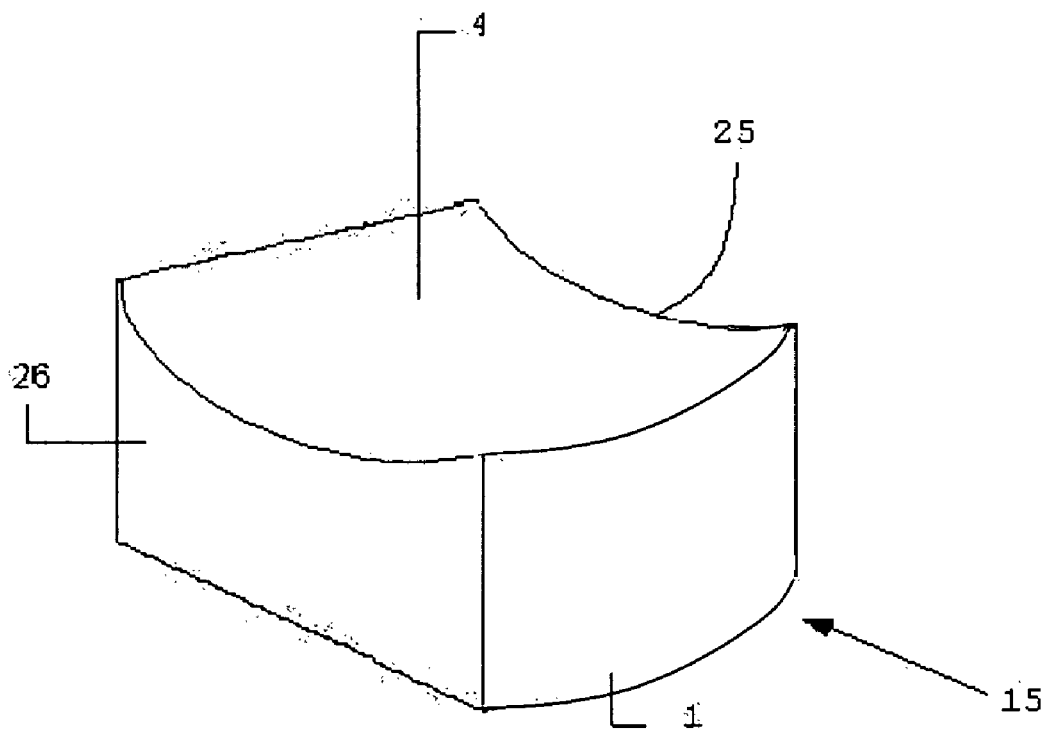
FIG. 40 is a perspective view of one embodiment of the present invention illustrating a concave depression in the upper surface of the slab of FIG. 38A.
Figure 41:
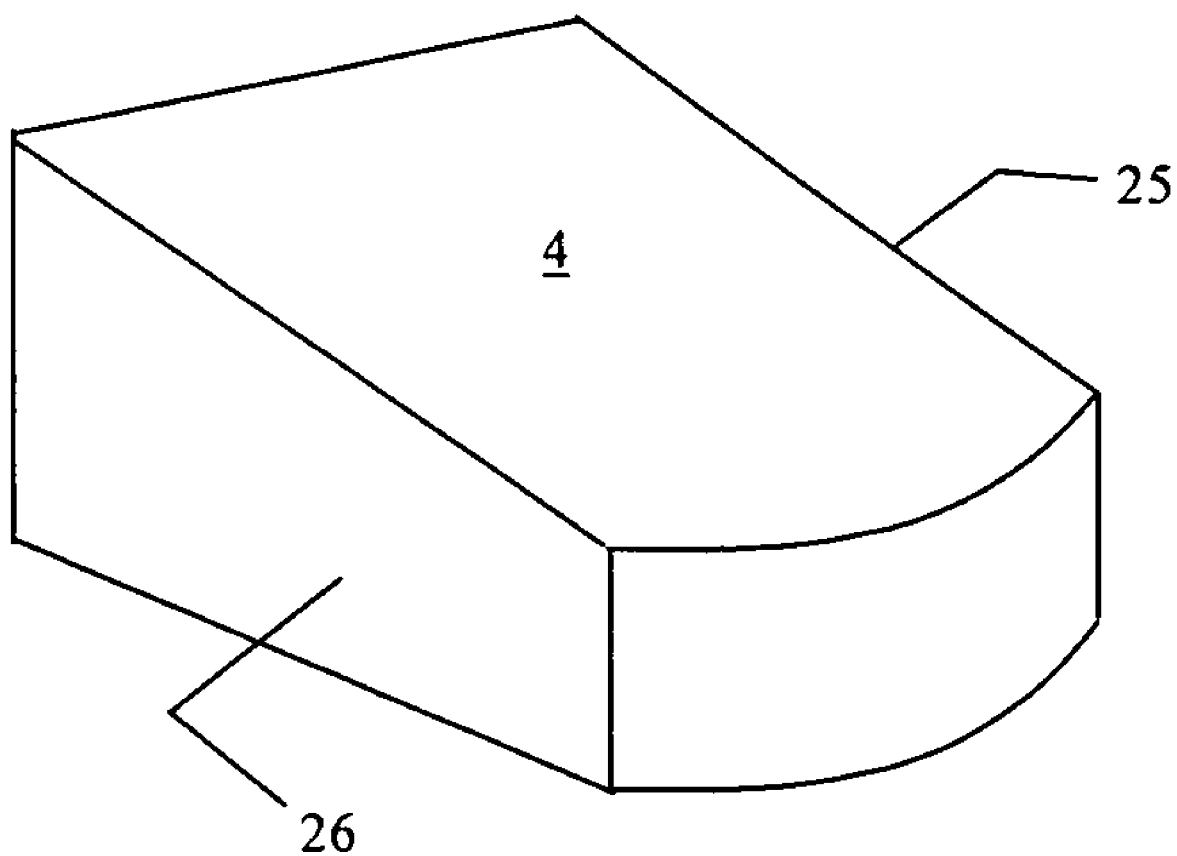
FIG. 41 is a perspective view of FIG. 39 with a slant on the upper surface.

In other alternative embodiments, the upper surfaces of the orthopedic appliances may not be parallel to the bottom surfaces. The upper surface may also be concaved or have a contour adapted to fit a portion of a toe, as illustrated in FIG. 40. The surface may also be slanted, for example, in a medial to lateral direction, as shown in FIG. 41. Some embodiments of the invention may have a combination of the features illustrated in FIGS. 40 and 41, i.e., a concave or contoured top surface that is also slanted.

As noted above, stability of the foot can be improved by raising the big toe at a proper height. One of ordinary skill in the art would appreciate that the proper height will depend on the sizes of the individuals. In general, the appliance 15 preferably has a height between 1-10 mm, more preferable between 4-6 mm.

In accordance with some embodiments of the invention, the appliance 15 may be adhered along the lower surface 1 to a planar surface of footwear where the hallux normally rests. That is, the orthopedic appliances described above, such as those shown in FIGS. 38-41, may be formed as an integral part of footwear, such as a sole, a slipper, a sandal, and the like. In accordance with other embodiments of the slab 15 also may be temporarily adhered to the hallux along the upper surface 4. Furthermore, orthopedic appliances as shown in FIGS. 38-41 may also include a fastener to facilitate resting the big toe on the appliances, as described with reference to FIGS. 21-26.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An orthopedic appliance, comprising a slab configured to be placed underneath a big toe forward of and not extending under a head of a first metatarsal, and wherein the slab has a predetermined height and is configured to deflect a proximal phalanx upwardly relative to the first metatarsal, wherein the slab has a top surface for supporting the big toe, a bottom surface, and four side surfaces, wherein a first side surface among the four side surfaces is disposed proximate a boundary between the big toe and the second toe during use, and a second side surface opposite the first side surface is disposed proximate a side edge of a footwear during use, wherein each of the four side surfaces is at least 1 mm high, and wherein the slab is attached to the footwear.

2. The orthopedic appliance of claim 1, wherein the predetermined height is between 1-10 mm.

3. The orthopedic appliance of claim 1, wherein the predetermined height is between 4-6 mm.

4. The orthopedic appliance of claim 1, wherein the top surface of the slab is non-planar.

5. The orthopedic appliance of claim 1, wherein the top surface and the bottom surface of the slab are not parallel.

6. The orthopedic appliance of claim 1, wherein the slab is an integral part of an article of footwear.

7. The orthopedic appliance of claim 1, further comprising a fastener configured to secure the big toe to the slab.

8. The orthopedic appliance of claim 1, wherein the footwear is an insole.

9. The orthopedic appliance of claim 1, wherein the footwear is a shoe or a sandal.

10. A method for improving stability of a foot during ambulation, comprising:

placing an orthopedic appliance, comprising a slab having a predetermined height, under a big toe such that the orthopedic appliance is located forward of and does not extend under a head of a first metatarsal of the big toe, wherein the slab has a top surface for supporting the big toe, a bottom surface, and four side surfaces, wherein a first side surface among the four side surfaces is disposed proximate a boundary between the big toe and the second toe during use, and a second side surface opposite the first side surface is disposed proximate a side edge of a footwear during use, wherein the four side surfaces are substantially perpendicular to the bottom surface and each of the four side surfaces is at least 1 mm high; and deflecting a proximal phalanx upwardly relative to the first metatarsal.

11. The method of claim 10, wherein the predetermined height is between 1-10 mm.

12. The method of claim 10, wherein the predetermined height is between 4-6 mm.

13. The orthopedic appliance of claim 10, wherein the top surface of the slab is non-planar.

14. The method of claim 10, wherein the top surface and the bottom surface of the orthopedic appliance are not parallel.

15. The method of claim 10, wherein the orthopedic appliance further comprises a fastener.

* * * * *